(12) United States Patent
Renke

(10) Patent No.: US 9,308,082 B2
(45) Date of Patent: Apr. 12, 2016

(54) OCULAR COLLAR STENT FOR TREATING NARROWING OF THE IRIDEOCORNEAL ANGLE

(71) Applicant: RegenEye, L.L.C., Point Roberts, WA (US)

(72) Inventor: Peter Renke, Vancouver (CA)

(73) Assignee: RegenEye, L.L.C., Point Roberts, WA (US)

( * ) Notice: Subject to any disclaimer, the term of this patent is extended or adjusted under 35 U.S.C. 154(b) by 298 days.

(21) Appl. No.: 13/960,416

(22) Filed: Aug. 6, 2013

(65) Prior Publication Data

US 2014/0046437 A1    Feb. 13, 2014

Related U.S. Application Data

(60) Provisional application No. 61/680,453, filed on Aug. 7, 2012.

(51) Int. Cl.
*A61F 9/007* (2006.01)
*A61F 2/14* (2006.01)
*A61F 2/82* (2013.01)

(52) U.S. Cl.
CPC ............... *A61F 2/14* (2013.01); *A61F 9/00781* (2013.01); *A61F 2/82* (2013.01)

(58) Field of Classification Search
CPC .......... A61F 2/14; A61F 2/82; A61F 9/00781
See application file for complete search history.

(56) References Cited

U.S. PATENT DOCUMENTS

| | | | |
|---|---|---|---|
| 4,722,724 A | 2/1988 | Schocket | |
| 5,318,047 A | 6/1994 | Davenport et al. | |
| 5,354,331 A | 10/1994 | Schachar | |
| 5,465,737 A | 11/1995 | Schachar | |
| 6,117,170 A | 9/2000 | Batdorf, Sr. | |
| 6,152,142 A | 11/2000 | Tseng | |
| 6,197,056 B1 | 3/2001 | Schachar | |

(Continued)

FOREIGN PATENT DOCUMENTS

| | | | |
|---|---|---|---|
| CA | 2178478 A1 | 6/1995 | |
| EP | 1598417 A1 | 11/2005 | |

(Continued)

OTHER PUBLICATIONS

Croft et al., "Accommodation and Presbyopia," International Ophthalmology Clinics, Spring 2001, pp. 33-46, 41(2).

(Continued)

*Primary Examiner* — Philip R Wiest
*Assistant Examiner* — Benjamin Klein
(74) *Attorney, Agent, or Firm* — The Webb Law Firm

(57) ABSTRACT

An ocular stent for insertion in an anterior chamber of an eye is provided. The stent facilitates the restoration of the structure of an irideocorneal angle of the anterior chamber for treating structural changes from ocular aging. The stent includes an annular body sized to fit in the irideocorneal angle of the eye. The body includes: an anterior portion configured to contact a surface of a transition zone between a trabecular meshwork and a corneal endothelium of the eye; a posterior portion configured to contact a peripheral iris of the eye; and a central portion connecting the anterior portion and the posterior portion of the body. A method for stabilizing the irideocorneal angle of the anterior chamber using a stent is also disclosed herein.

11 Claims, 10 Drawing Sheets

(56) References Cited

U.S. PATENT DOCUMENTS

| | | | |
|---|---|---|---|
| 6,494,910 | B1 | 12/2002 | Ganem et al. |
| 6,616,692 | B1 | 9/2003 | Glick et al. |
| 6,682,560 | B1 | 1/2004 | Baikoff |
| 6,849,090 | B2 | 2/2005 | Nigam |
| 6,991,650 | B2 | 1/2006 | Zdenek et al. |
| 7,273,475 | B2 | 9/2007 | Tu et al. |
| 7,297,130 | B2 | 11/2007 | Bergheim et al. |
| 7,708,711 | B2 | 5/2010 | Tu et al. |
| 7,828,844 | B2 | 11/2010 | Marmo et al. |
| 8,005,526 | B2 | 8/2011 | Martin et al. |
| 8,167,939 | B2 | 5/2012 | Silvestrini et al. |
| 8,197,540 | B2 | 6/2012 | Basoglu et al. |
| 8,366,653 | B2 | 2/2013 | Shareef et al. |
| 8,409,277 | B2 | 4/2013 | Griffis, III et al. |
| 2004/0015232 | A1 | 1/2004 | Shu et al. |
| 2004/0193262 | A1 | 9/2004 | Shadduck |
| 2005/0186672 | A1 | 8/2005 | Mahadeorao et al. |
| 2006/0041308 | A1 | 2/2006 | Nichamin |
| 2006/0074487 | A1 | 4/2006 | Gilg |
| 2007/0049952 | A1 | 3/2007 | Weiss |
| 2007/0219632 | A1 | 9/2007 | Castillejos |
| 2008/0027304 | A1 | 1/2008 | Pardo et al. |
| 2008/0091224 | A1 | 4/2008 | Griffis, III et al. |
| 2008/0091266 | A1 | 4/2008 | Griffis, III et al. |
| 2008/0243247 | A1 | 10/2008 | Poley et al. |
| 2010/0068141 | A1 | 3/2010 | Kaushal et al. |
| 2010/0114303 | A1 | 5/2010 | Su et al. |
| 2010/0137981 | A1 | 6/2010 | Silvestrini et al. |
| 2010/0191176 | A1 | 7/2010 | Ho et al. |
| 2010/0262233 | A1 | 10/2010 | He |
| 2010/0286770 | A1 | 11/2010 | Tomalla et al. |
| 2011/0118649 | A1* | 5/2011 | Stegmann et al. ........... 604/8 |
| 2013/0103143 | A1 | 4/2013 | Jacobson et al. |
| 2014/0107776 | A1 | 4/2014 | Williamson et al. |

FOREIGN PATENT DOCUMENTS

| | | | |
|---|---|---|---|
| WO | 02102274 | A2 | 12/2002 |
| WO | 03077794 | A2 | 9/2003 |
| WO | 2004012619 | A2 | 2/2004 |
| WO | 2008039397 | A2 | 4/2008 |
| WO | 2010093468 | A1 | 8/2010 |
| WO | 2011103555 | A2 | 8/2011 |

OTHER PUBLICATIONS

Croft et al., "The zonula, lens, and circumlental space in the normal iridectomized rhesus monkey eye," Investigative Ophthalmology and Visual Science. 2006, pp. 1087-1095, (47).

Croft et al., "Surgical intervention and accommodative responses: I. Centripetal ciliary body, capsule, and lens movement in rhesus monkeys of various ages," Investigative Ophthalmology and Visual Science. 2008, pp. 5484-5494, (49).

Wasielewski et al., "Surgical intervention and accommodative responses, II. Forward ciliary body accommodative movement is facilitated by zonular attachments to the lens capsule," Investigative Ophthalmology and Visual Science. 2008, pp. 5495-5502, (49).

Croft et al., "Age-related changes in centripetal ciliary body movement relative to centripetal lens movement in monkeys," Experimental Eye Research. 2009, pp. 824-832, (89) (20 pp.)

Lutjen-Drecoll et al., "Morphology and accommodative function of the vitreous zonule in human and monkey eyes," Investigative Ophthalmology and Visual Science. 2010, pp. 1554-1564, 51(3).

Croft et al., "Accommodative movements of the vitreous membrane, choroid and sclera in young and presbyopic human and nonhuman primate eyes," Investigative Ophthalmology and Visual Science. 2013, pp. 5049-5058, vol. 54.

Croft et al., "Extralenticular and lenticular aspects of accommodation and presbyopia in human versus monkey eyes." Investigative Ophthalmology and Visual Science. 2013, pp. 5035-5048, (54).

Croft et al., "Accommodative movements of the lens/capsule in relation to the vitreous face and aging," ARVO Abstract #386. 2013.

Neider et al., "In vivo videography of the rhesus monkey accommodative apparatus. Age-related loss of ciliary muscle response to central stimulation," Archives of Ophthalmology. 1990, pp. 69-74, (108)—Abstract.

Tamm et al., "Age-related changes of the human ciliary muscle. A quantitative morphometric study," Mechanisms of Ageing and Development. 1992, pp. 209-221, (62).

Tamm et al., "Age-related loss of ciliary muscle mobility in the rhesus monkey: role of the choroid," Archives of Ophthalmology. 1992, pp. 871-876, (110).

Croft et al., "Aging effects on accommodation and outflow facility responses to pilocarpine in humans," Archives of Ophthalmology. 1996, pp. 586-592, (114) Abstract.

Glasser et al., "Ultrasound biomicroscopy of the aging rhesus monkey ciliary region," Optometry and Vision Science. 2001, pp. 417-424, (78).

Glasser et al., "Presbyopia and the optical changes in the human crystalline lens with age," Vision Research. 1998, pp. 209-229, 38(2) Abstract.

Glasser et al., "Biometric, optical and physical changes in the isolated human crystalline lens with age in relation to presbyopia," Vision Research. 1999, pp. 1991-2015, (39).

Croft et al., "Accommodative movements of the choroid in the region of the optic nerve in young and old eyes," ARVO Abstract #. 2014.

He et al., "Full-Field Accommodation in Rhesus Monkeys Measured Using Infrared Photorefraction," Visual Psychophysics and Physiological Optics. Jan. 2012, pp. 215-223, vol. 53, No. 1.

Lanchares et al., "Hyperelastic modelling of the crystalline Lens: Accommodation and presbyopia," Journal of Optometry. 2012, pp. 110-120, (5).

Barraquer et al., "Human Lens Capsule Thickness as a Function of Age and Location along the Sagittal Lens Perimeter," Investigative Ophthalmology and Visual Science. May 2006, pp. 2053-2060 vol. 47, No. 5.

Chung et al., "Transient anterior subcapsular vacuolar change of the crystalline lens in patients after posterior chamber phakic intraocular lens implantation," BMC Ophthalmology. 2013, 13:61 4 pages.

Dubbelman et al., "Changes in shape of the aging human crystalline lens with accommodation," Vision Research, 2005, pp. 117-132, (45).

Michael et al., "The ageing lens and cataract: a model of normal and pathological ageing," The Royal Society of Biological Sciences, 2011, pp. 1278-1292, (366).

Kasthurirangan et al., "MRI study of the changes in crystalline lens shape with accommodation and aging in humans," Journal of Vision, Mar. 2011, pp. 1-16, 11(3):19.

Dubbelman et al., "The shape of the human lens: curvature, equivalent refractive index and the lens paradox," Vision Research, 2001, pp. 1867-11877, (41).

Strenk et al., "In vivo MRI . . . visualizing the haptics," Eyeworld, Sep. 2007, 8 pages.

Ni et al., "Objective evaluation of the changes in the crystalline lens during accommodation in young and presbyopic populations using Pentacam HR system," Int. J. Ophthalmol. Dec. 2011, pp. 611-615, vol. 4, No. 6.

Hollman et al., "Mapping elasticity in human lenses using bubble-based acoustic radiation force," Experimental Eye Research, Dec. 2007, pp. 890-893, 85(6) 4 pages.

Iyamu et al., "Age, gender, corneal diameter, corneal curvature and central corneal thickness in Nigerians with normal intra ocular pressure," Journal of Optometry, 2012, pp. 87-97.

Augusteyn et al., "Human ocular biometry," Experimental Eye Research, 2012, pp. 70-75, (102).

Gabelt et al., "Aqueous Humor Dynamics and Trabecular Meshwork and Anterior Ciliary Muscle Morphologic Changes with Age in Rhesus Monkeys," Investigative Ophthalmology and Visual Science. May 2003, pp. 2118-2125 vol. 44, No. 5.

Huang et al., "Association of biometric factors with anterior chamber angle widening and intraocular pressure reduction after uneventful phacoemulsification for cataract," J. Cataract Refract. Surg. Jan. 2012, pp. 108-116, 38(1) 19 pages.

(56) References Cited

OTHER PUBLICATIONS

Shao et al., "Simultaneous real-time imaging of the ocular anterior segment including the ciliary muscle during accommodation," Biomedical Optics Express, Mar. 2013, vol. 4, No. 3 pp. 466-480.
Bell et al., "Age and Positional Effect on the Anterior Chamber Angle: Assessment by Ultrasound Biomicroscopy," ISNR Ophthalmology, Hindawi Publishing, 2013, 5 pages, vol. 2013, Article ID 706201.
Vossmerbaeumer et al., "Width of the anterior chamber angle determined by OCT, and correlation to refraction and age in German working population: the MIPH Eye&Health Study," Graefes Arch. Clin. Exp. Ophthalmol., 2013, pp. 2741-2746, (251).
Ruggeri et al., "Biometry of the Ciliary Muscle during Dynamic Accommodation assessed with OCT," SPIE the International Society for Optics and Photonics, 2014, 7 pages, vol. 8930, 89300W.
Richdale, Kathryn, "Ocular and Refractive Considerations for the Aging Eye," VisionCare Education, Feb. 2009, 6 pages.
Munch et al., "Small, Hard Macular Drusen and Peripheral Drusen: Associations with AMD Genotypes in the Inter99 Eye Study," Investigative Ophthalmology and Visual Science. May 2010, pp. 2317-2321, vol. 51, No. 5.
Li et al., "Refractive Error and Risk of Early or Late Age-Related Macular Degeneration: A Systematic Review and Meta-Analysis," PLOS ONE, Mar. 2014, 11 pages, vol. 9, Issue 3.
Wong et al., "Refractive Errors and 10-Year Incidence of Age-Related Maculopathy," Investigative Ophthalmology and Visual Science. Sep. 2013, pp. 2869-2873, vol. 43, No. 9.
Mo et al., "Risk factor analysis of 167 patients with high myopia," Int. J. Ophthalmol., pp. 80-82, 3(1), 2010.
Lipner, Maxine, "Five-Year refractive changes in an adult population," Eyeworld, Sep. 2005, 3 pages.
Galgauskas et al., "Age-related changes in corneal thickness and endothelial characteristics," Clinical Interventions in Aging, 2013:8, pp. 1445-1450.
Stolberg et al., "Can Shear Stress Direct Stem Cell Fate?" American Institute of Chemical Engineers, Feb. 2009, pp. 10-19.
Sikder et al., "Complications of NewColorIris implantation in phakic eyes: a review," Clinical Ophthalmology, 2011:5, pp. 435-438.
Doran, Marianne, "Iris Implants Advance—but Face Continuing Challenges," EYENET, Feb. 2013, pp. 29-31.
Neal / Conference Syllabus, International Society of Presbyopia, London, Sep. 12, 2014.
Asrani et al., "Detailed Visualization of the Anterior Segment Using Fourier-Domain Optical Coherence Tomography," Arch Ophthalmol., Jun. 2008, pp. 765-771, vol. 126, No. 6.
Bernal et al., "Evidence for Posterior Zonular Fiber Attachment on the Anterior Hyaloid Membrane," Investigative Ophthamology & Visual Science, Nov. 2006, pp. 4708-4713, vol. 47, No. 11.
Burd et al., "Numerical Modelling of Accomodation and Presbyopia (1999-2002)," University of Oxford Civil Engineering Research, 2002, 2 pages.
Cohen et al., "Mechanical control of stem cell differentiation," Stembook, Oct. 31, 2008, pp. 1-16.
Correa et al., "Ultrasound Biomicroscopy of the Anterior Ocular Segment (Chapter 106)," Duane's Ophthamology on CD-ROM, 2006, 12 pages.
Croft et al., "Accommodative Ciliary Body and Lens Function in Rhesus Monkeys, I: Normal Lens, Zonule, and Ciliary Process Configuration in the Iridectomized Eye," Investigative Ophthamology and Visual Science, Mar. 2006, pp. 1076-1085, vol. 47, No. 3.
Dooley et al., "Changes in intraocular pressure and anterior segment morphometry after uneventful phacoemulsification cataract surgery," Eye, 2010, pp. 519-527, vol. 24.
Eghrari et al., "Fuchs' Corneal Dystrophy," Expert Rev Ophthalmol., Apr. 2010, pp. 147-159, vol. 5, No. 2.
Farrell, "Hydrophilic vs hydrophobic: which is the better option?: Measuring IOL success in broader terms," Ophthalmology Times Europe, Sep. 1, 2008, 6 pages, vol. 4, Issue 7.

Freddo et al., "Anatomy of the Ciliary Body and Outflow Pathways (Chapter 43)," Duane's Ophthalmology on CD-ROM, 2006, 12 pages.
"Glaucoma," Veterinary Vision, Inc., http://www.veterinaryvision.com/dvm-glaucoma.htm, accessed Apr. 29, 2012, 2 pages.
"Glaucoma Facts and Stats," Glaucoma.org, http://www.glaucoma.org/glaucoma/facts-statistics/glaucoma-facts-and-stats.php, accessed Jun. 1, 2012, 4 pages.
Grozdanic et al. "Functional and Structural Changes in a Canine Model of Hereditary Primary Angle-Closure Glaucoma," Investigative Ophthamology and Visual Science, Jan. 2010, pp. 255-263, vol. 51, No. 1.
Johansson, "Clinical consequences of acrylic intraocular lens material and design: Nd:YAG-laser capsulotomy rates in 3×300 eyes 5 years after phacoemulsification," Br J Ophthalmol, 2010, pp. 450-455, vol. 94.
Kang et al., "Comparison of clinical results between heparin surface modified hydrophilic acrylic and hydrophobic acrylic introcular lens" European of Journal of Ophthalmology, 2008, pp. 1-7, vol. 18.
Kawamorita et al., "Relationship between ciliary sulcus diameter and anterior chamber diameter and corneal diameter," J Cataract Refract Surg, 2010, pp. 617-624, vol. 36.
Keane et al., "Clinical Applications of Long-Wavelength (1,000-nm) Optical Coherence Tomography," Ophthalmic Surgery, Lasers & Imaging, 2011, pp. S67-S74, vol. 42, No. 4 (Suppl.).
Kent, "IOLs: How Much Does Material Matter?" Review of Ophthalmology, Apr. 17, 2008, 8 pages.
Kent, "IOP: Managing the Fluctuation Factor," Review of Ophthalmology, Jun. 13, 2011, 5 pages.
Lanzetta et al., "Use of capsular tension ring in a phacoemulsification, indications and technique," Ophthalmology Practice, 2002, pp. 333-337, vol. 50, Issue 4.
Liu, "Anatomical Changes of the Anterior Chamber Angle With Anterior-Segment Optical Coherence Tomography," Arch Ophthalmol, Dec. 2008, pp. 1682-1686, vol. 126, No. 12.
Lombardo et al., "Analysis of intraocular lens surface properties with atomic force microscopy," J Cataract Refract Surg, Aug. 2006, pp. 1378-1384, vol. 32.
Lowe, "Anterior lens displacement with age," Brit. J. Ophthal., 1970, pp. 117-121, vol. 54.
Luthe, "A Closer Look at Premium Lenses," Ophthalmology Management, May 2009, 8 pages.
McGowan et al., "Stem cell markers in the human posterior limbus and corneal endothelium of unwounded and wounded corneas." Mol. Vis, Oct. 18, 2007, pp. 1984-2000, vol. 13.
McLeod et al., "A dual optic accommodating foldable introcular lens," British Journal of Ophthalmology, Sep. 2003, pp. 1083-1085, vol. 87, No. 9.
Mills, "Trabeculectomy: a retrospective long-term follow-up of 444 cases," British Journal of Ophthalmology, 1981, pp. 790-795, vol. 65.
Moses et al., "The trabecular mesh: a mathematical analysis," Invest. Ophthalmol. Vis. Sci., Dec. 1980, pp. 1490-1497, vol. 19, No. 12.
Mottola, "Calculating the Sagitta of an Arc," Lutherie Information Website for builders of stringed musical instruments, Apr. 5, 2009, 4 pages.
Moyer, "Anterior Segment Optical Coherence Tomography (AS-OCT)," Ophthalmic Photographers Society, 2011-2012, 4 pages.
"Online Resources of Ophthalmology" www.eophtha.com/eophtha/anatomyoflens3.html, 2011, 5 pages.
Pinchuk et al., "Medical applications of poly(styrene-block-isobutylene-block-styrene) ("SIBS")," Biomaterials, 2007, pp. 448-460, vol. 29, No. 4.
Read et al., "The Topography of the Central and Peripheral Cornea," Investigative Ophthalmology & Visual Science, Apr. 2006, pp. 1404-1415, vol. 47, No. 4.
Roberts, "Patients at Risk: Myriad factors influence the way we study the development of glaucoma—and treat it," Optometric Management, Jun. 2006, 4 pages.
Schachar et al., "The Mechanism of Human Accommodation As Analyzed by Nonlinear Finite Element Analysis," Compr. Ther., 2001, pp. 122-132, vol. 27, No. 2.
Secker et al. "Limbal epithelial stem cells of the cornea," Stembook, 2009, 17 pages.

(56) References Cited

OTHER PUBLICATIONS

Solomon, "Aqueous Humor Dynamics." 2002, 17 pages.
Streeten, "Anatomy of the Zonular Apparatus (Chapter 14)," Duane's Ophthalmology on CD-ROM, 2006, 20 pages.
Stuart, "In Glaucoma, Devices Go Eye-to-Eye With Drugs," Start-up, Sep. 1, 2010, 11 pages, vol. 15, No. 8.
Thomas, "Use Specular Microscopy to Diagnose Corneal Disease," Review of Optometry, Jun. 15, 2009, 4 pages.
TradeKorea.com, "IOL, CTR," accessed Apr. 29, 2012, 3 pages.
Tsorbatzoglou et al. "Unravelling Accomodation Theories: Will We Ever Find the Real Answer?," Ophthalmology Times Europe, Jul. 1, 2008, 4 pages, vol. 4, No. 6.
Vecino, "Animal Models in the Study of Glaucoma: Past, Present and Future," Arch Soc Esp Oftalmol, 2008, pp. 517-520, vol. 83.
Yan et al. "Anterior Segment Variations with Age and Accomodation Demonstrated by Slit-Lamp-Adapted Optical Coherence Tomography," Ophthalmology, Dec. 2010, pp. 2301-2307, vol. 117, No. 12.
Yu et al., "Progenitors for the Corneal Endothelium and Trabeculer Meshwork: A Potential Source for Personalized Stem Cell Therapy in Corneal Endothelial Diseases and Glaucoma," Journal of Biomedicine and Biotechnology, 2011, 17 pages, vol. 2011.
Shao et al., Age-Related Changes in the Anterior Segment Biometry During Accommodation, Investigative Ophthalmology & Visual Science, 2015, 3522-3530, 56.

* cited by examiner

FIG. 3A
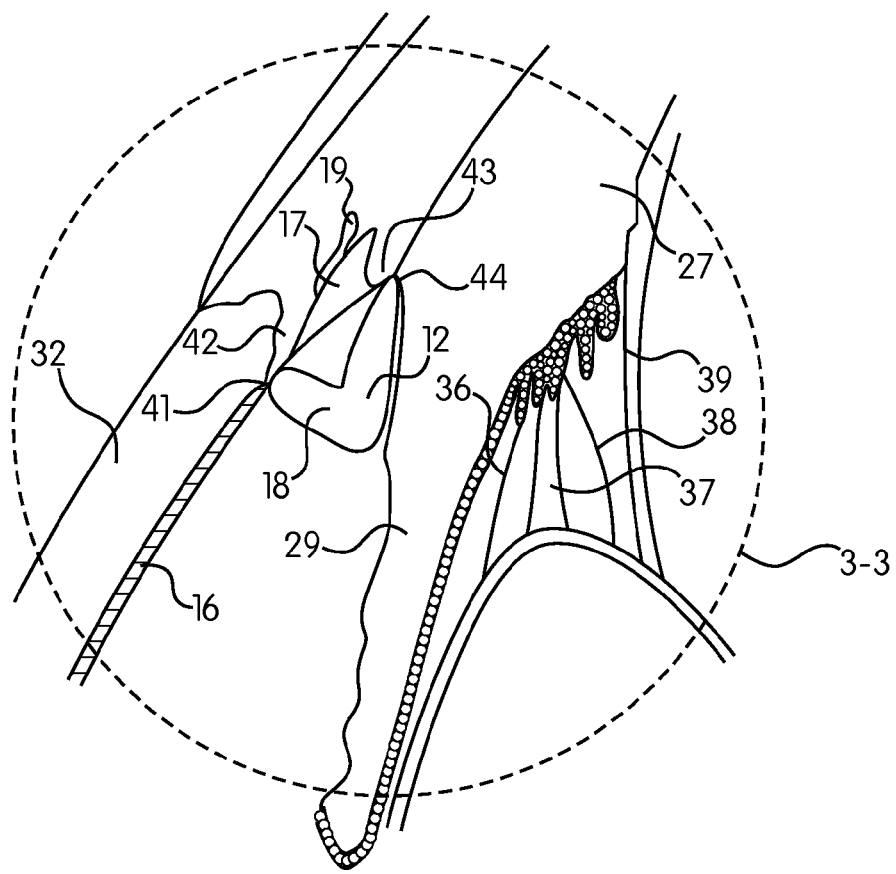
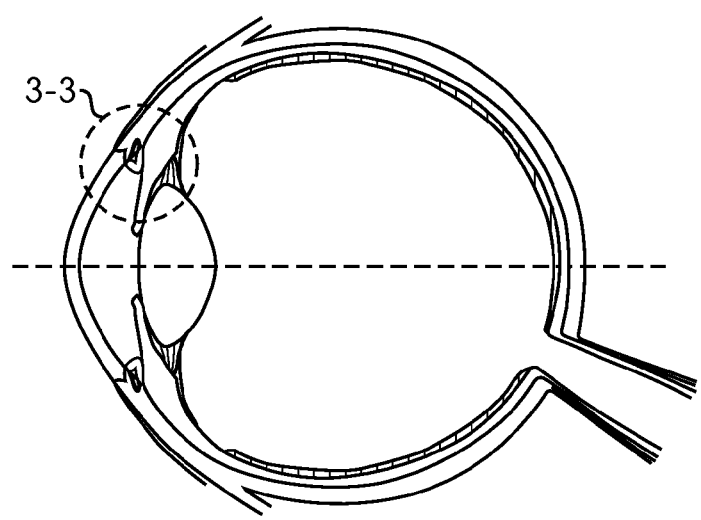
FIG. 3

Fig. 4A
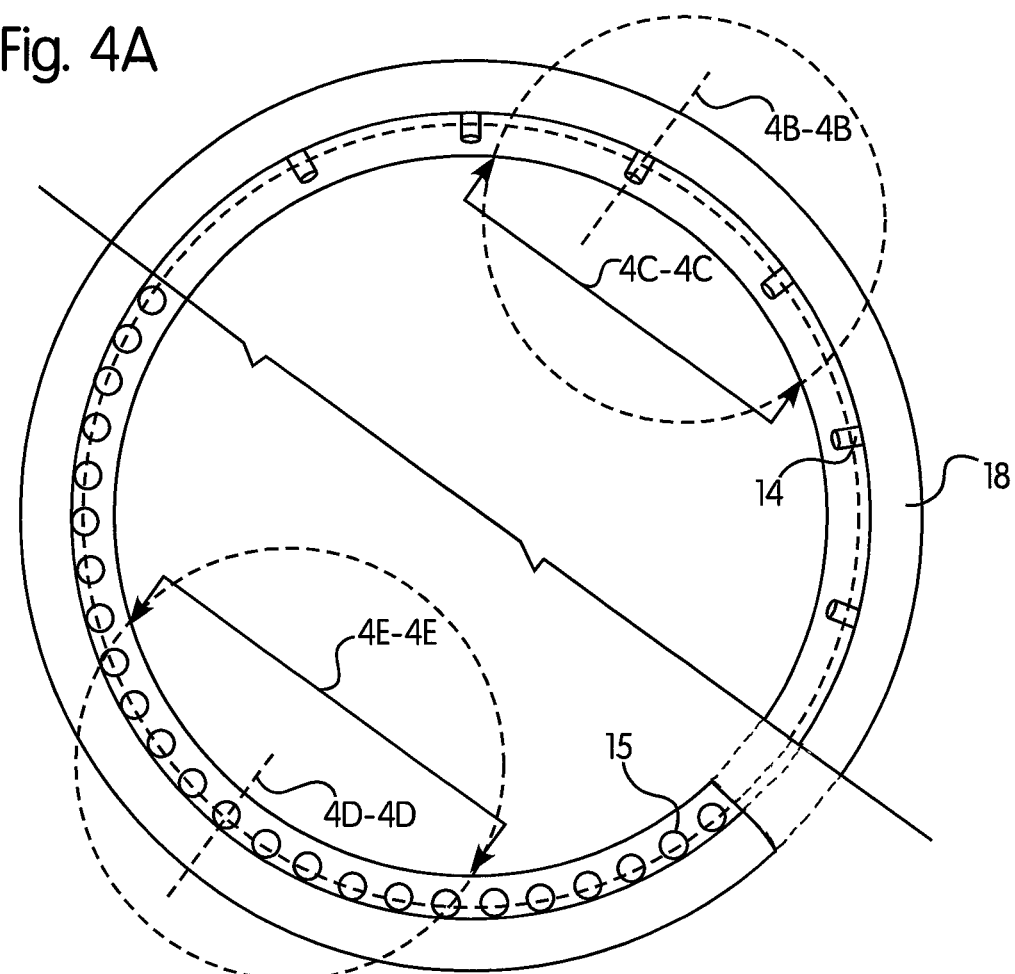
FIG. 4C
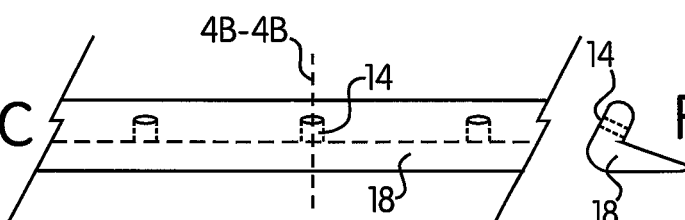
FIG. 4B
FIG. 4E
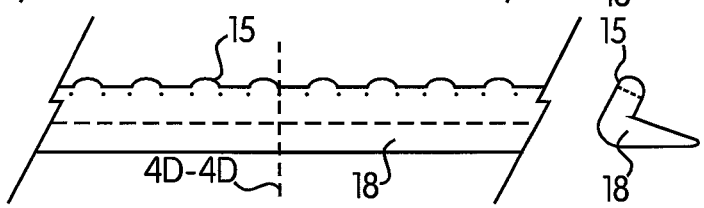
FIG. 4D

FIG. 5A
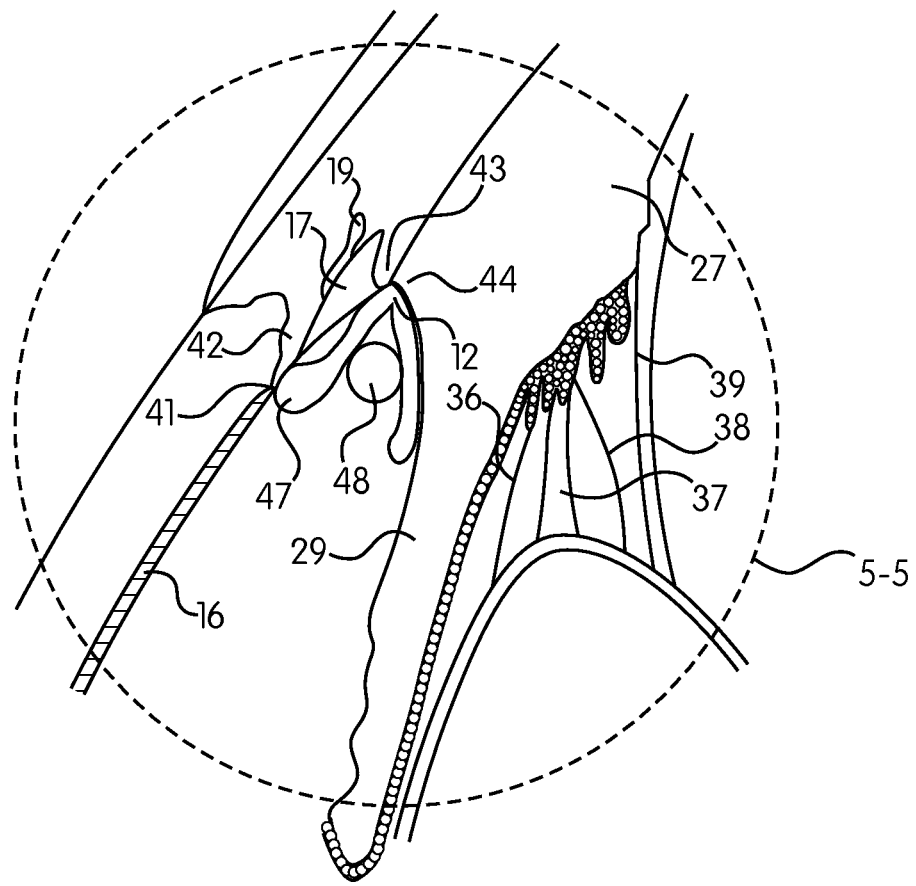
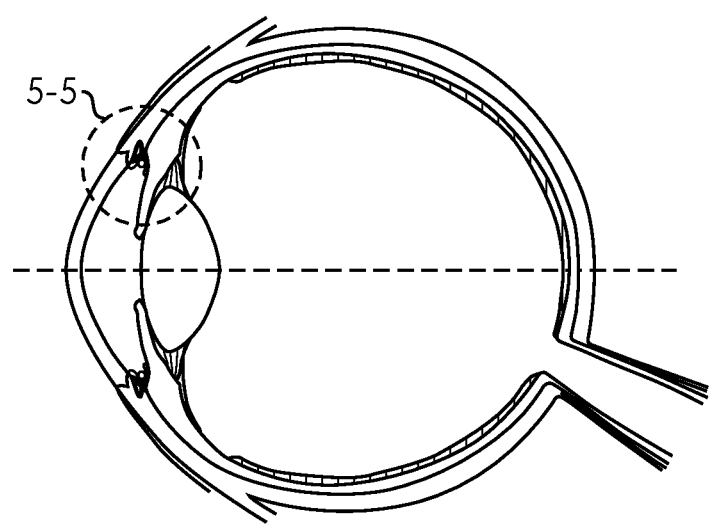
FIG. 5

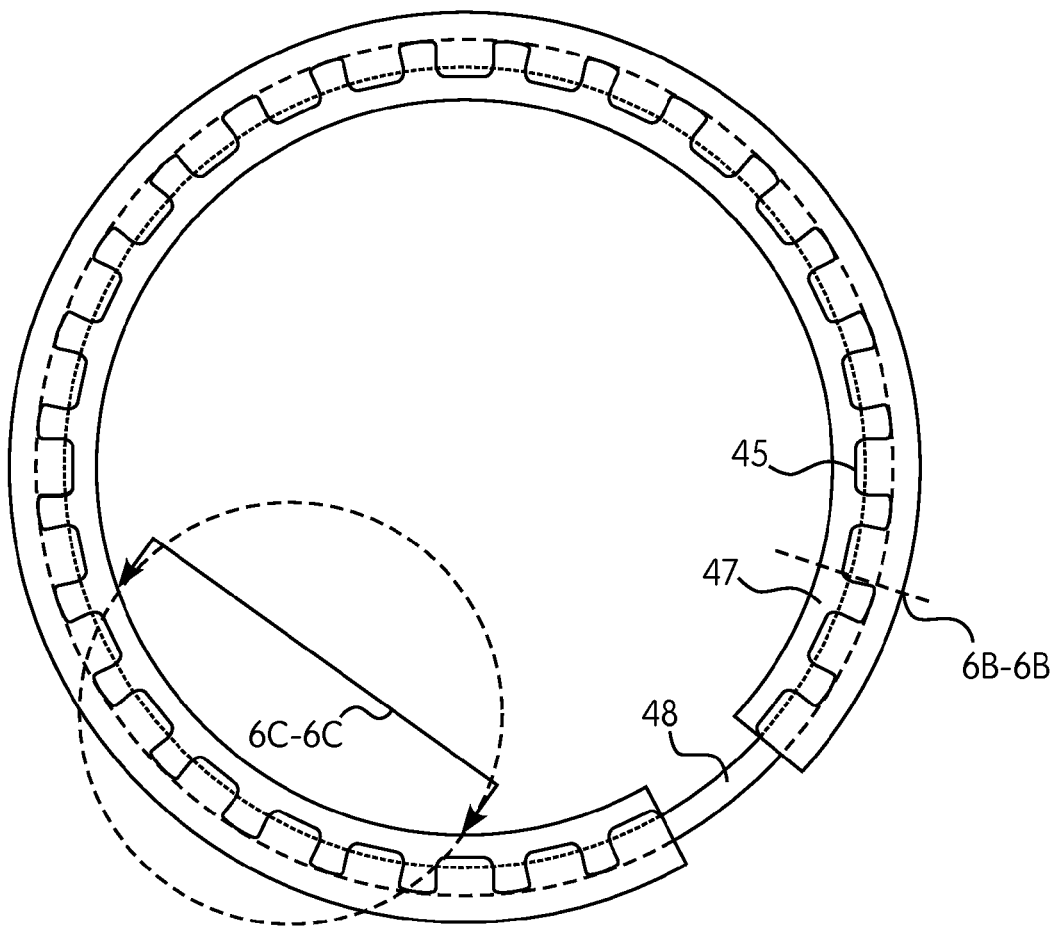
FIG. 6A
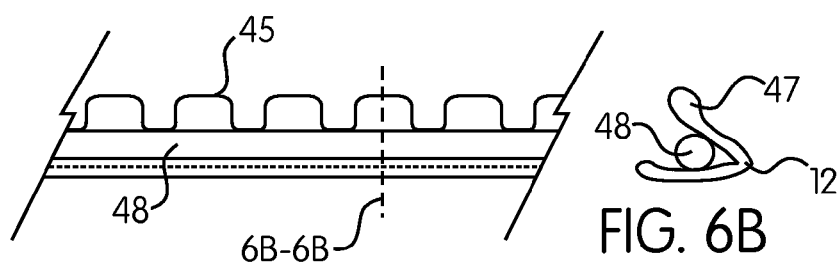
FIG. 6C
FIG. 6B

FIG. 7A
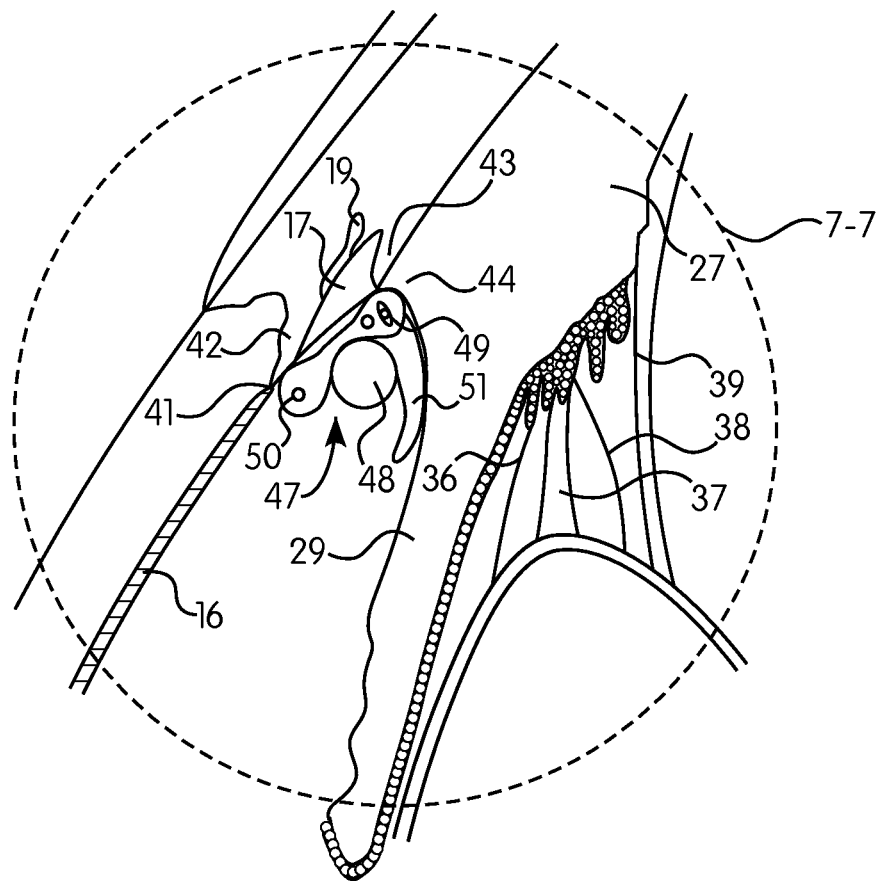
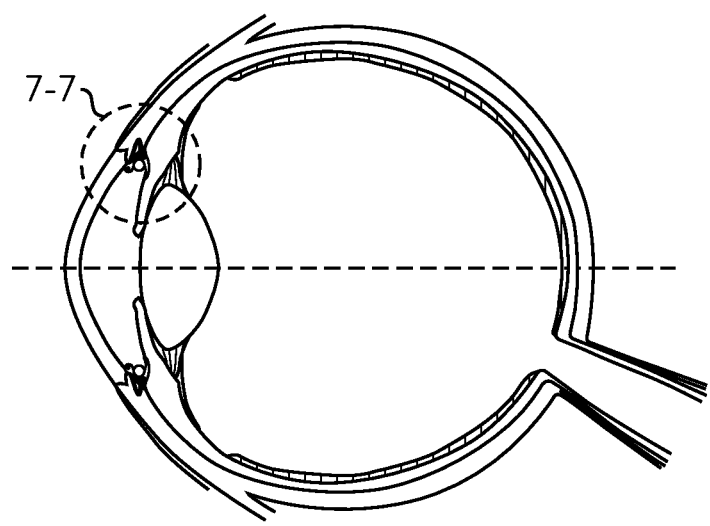
FIG. 7

OCULAR COLLAR STENT FOR TREATING NARROWING OF THE IRIDEOCORNEAL ANGLE

CROSS REFERENCE TO RELATED APPLICATION

This application claims priority to U.S. Provisional Patent Application No. 61/680,453 filed on Aug. 7, 2012, which is hereby incorporated by reference in its entirety

BACKGROUND OF THE INVENTION

1. Field of the Invention

This invention relates broadly to a structure for insertion in the anterior mammalian eye for treatment related to natural, predictable aging changes. More particularly the invention relates to a surgically implanted device for the human eye. The device provides structural support to specific ocular anatomy as a means to counteract changes naturally brought about by aging.

2. Description of the Related Art

All human eyes go through physical changes as a result of the normal aging processes. These changes affect various structures of the eye. The human eye has three chambers. The largest is the vitreous chamber. It is filled with the gelatinous material of the vitreous body. This material fills the eye and principally serves to maintain the shape of the eye. It also plays a role in accommodation to anchor the posterior lens attachments and interact with induced forces. In front of the vitreous chamber are the posterior and anterior chambers. These chambers also play a role in maintaining the shape of the eye through the mechanism of balancing the production and drainage of aqueous humor. This fluid fills both chambers, which are separated by the iris. The pupil is the area of communication between the two chambers. The aqueous humor is produced by the ciliary body in the posterior chamber and then circulates forward through the pupil to the anterior chamber. The fluid then slowly filters through the annular structure of the trabecular meshwork and its distal system. The anterior chamber is demarked by the cornea and iris. The boundaries of the posterior chamber are the iris and anterior lens capsule. The posterior chamber peripherally reaches to the ciliary body, which is the location of the musculature and apparatus attachment responsible for accommodation.

Accommodation involves constriction and relaxation of the ciliary muscles to achieve the control of focus. The process of accommodation is naturally controlled by the brain. It is an automatic process that results in clear vision by manipulation of the lens shape and position to focus light on the retina. The eye goes through a predictable degradation of accommodation with aging. The focusing apparatus becomes progressively more flaccid over time. The musculature and feedback mechanism remain intact, but the ability to actuate change and focus diminishes throughout life, until it is essentially totally ineffective. This process is known as presbyopia. The youthful eye has excessive ability to accommodate in the order of tenfold of what is generally required. This surplus erodes over time, and usually reaches the threshold of being initially problematic at 40 to 45 years old. The degradation continues to progress and usually renders the eye with complete inability to sustain any near focus by the age of 60. This is a very relevant juncture with respect to the aging process of the eye and subsequent prevalence of various disease processes as they manifest. These predictable changes result in an anterior shifting of the lens and focusing apparatus. The lens and apparatus are attached by micro ligaments known as zonules. The zonules become progressively more flaccid with aging. The cause of this increased flaccidity is likely two fold. The zonules simply stretch over time due to perpetual use. This stretching is likely a contributing factor, but aging changes to the actual lens is responsible for the majority of change. These aging changes eventually manifest as cataracts. Cataract development is a predictable and understood change to the aging eye. The matrix of the crystalline lens becomes cloudy and impairs vision. This typically becomes problematic enough to require cataract surgery between the ages of 70 to 80. As part of the process the lens stiffens, thickens, and subsequently increases in diameter. This increase in diameter results in outward displacement of the zonule attachments. The entire focusing system becomes relatively slack and displaces forward. The thickening of the lens also compounds these forward forces as the vitreous body pushes the structures from behind. Surgically removing the cataract becomes necessary and is common practice.

At the stage prior to surgery, the intact aged eye has to maintain function with very unfavourable displaced and compressed anatomy. The prevalence of various eye diseases begins to increase dramatically after the first five decades of life. These diseases include, but are not limited to, glaucoma, Fuchs' corneal dystrophy, and retinal detachments. These three diseases are discussed herein, as each disease relates to forward shifting anatomical changes. Presbyopia and refractive error are also discussed, but are not considered to be diseases.

Glaucoma is a disease which is diagnosed by evidence of vision loss or measured change to the optic nerve and the retinal nerve fiber layers. It is estimated that over 4 million Americans have glaucoma, but only half of the people who suffer from the disease are aware of their condition. Approximately 120,000 people are blind as a result of the disease. Glaucoma is the second leading cause of blindness in the world. Estimates put the total number of suspected cases of glaucoma at about 70 million worldwide. Glaucoma is a group of diseases that relate to intraocular pressure (TOP) and the aqueous humor fluid dynamics of the eye. It is a balance between the rate of aqueous production from the ciliary body in the posterior chamber and drainage via the trabecular meshwork and its distal system located in the anterior chamber. It is estimated that the ciliary body produces aqueous at an average rate of 2-3 micro liters per minute which translates into about 1.5 liters per year. There are variations in rates of production; however, these fluctuations are likely not as significant as the ability to drain the fluids, to balance pressure. The aging of the eye results in a predictable anterior shift of the structures posterior to the trabecular meshwork. This shift results in restriction of flow based on the structural change. Evidence of this shift is observed clinically when a cataract is surgically removed. On average, there is a 17% decrease in intraocular pressure (TOP), shortly after surgery. The anterior chamber angle instantly widens upon removal of the lens. The structure of the trabecular meshwork is able to open under these favourable changes. The trabecular meshwork is a mesh-like structure of tapering pores that direct the fluids into Schlemm's canal. The natural architecture of this porous tissue cannot perform its function well under compression. Glaucoma patients often undergo cataract surgery prematurely to take advantage of the drop in baseline IOP. Cataract surgery could be delayed or avoided in many cases where the need for the operation is driven by the pressure reduction aspects. The visual complications of natural aging cataracts are generally noticed by one's early sixties. Vision continues to decline typically requiring cataract surgery at ages ranging from early to mid seventies. The average life expectancy in the United States from birth is 78. It is more relevant to consider that the average life expectancy from an age of 63 is 20 years. Thus, a significant portion of the population does not live long enough to require cataract surgery based on vision needs.

Although glaucoma is a group of diseases, it can generally be classified into two categories: closed angle and open angle glaucoma. Closed angle glaucoma is a medical emergency when the angle is truly closed. This occurs when the peripheral iris occludes the trabecular meshwork. Topical and systemic pharmaceutical agents must be employed and often an emergency iridotomy is needed. An iridotomy involves making puncture-like openings through the iris without the removal of iris tissue. It is performed either with standard surgical instruments or a laser. The iridotomy allows for instant equalization of IOP between the anterior and posterior chamber.

Primary Open Angle Glaucoma (POAG) accounts for the majority of glaucoma cases. It presents with an apparently open drainage structure and often normal intraocular pressures. It is characterized by progressive optic neuropathy resulting in atrophy of the optic nerve and the nerve fiber layers. The disease process must have factors that are not apparent upon superficial anatomical observation and clinical IOP measurements. It is well documented that IOP fluctuates. Animal studies where IOP measuring probes have been implanted have demonstrated very dramatic results. Rabbit and monkey subjects produced TOP spikes in the order of 90 mmHg. This represents pressure almost six times normal values. This highlights the necessity of IOP clearing time for these spikes to maintain eye health. The eye must be able to sustain brief spikes in IOP. Sneezing and rubbing one's eyes would be examples of normal acute IOP spikes. Early POAG cases are likely, in part, the inability of the eye's drainage system to facilitate a safe pressure clearing time. In these open angle cases the trabecular meshwork structure would be initially compressed internally and out of superficial view. This coincides with the stage of rapid decline in loss of accommodation at the age of 50 to 60. This directly correlates to the age where the incidence of glaucoma dramatically increases. The angle is internally compressing in the periphery as the ciliary body and its structures shift forward. The angle and whole anterior chamber are narrowing. The farther forward the structures shift, the greater the zonular flaccidity. As this progresses there is less pulling on the anatomy adjacent to the trabecular meshwork, which is known to decrease IOP. The action of pilocarpine eye drops utilizes this mechanism to lower IOP. Pilocarpine also acts on the ciliary muscle and causes it to contract. When the ciliary muscle contracts, it opens the trabecular meshwork through increased tension on the scleral spur at the base of the trabecular meshwork. This narrowing trend becomes more apparent 10 to 20 years later with significant cataract development. The central thickening of the lens produces additional forward movement that is more evident on clinical observation.

In general the disease process is treated by isolated approaches to certain aspects of the disease. Pharmaceutical agents represent the primary form of treatment. They work on modulating production or drainage of the aqueous fluids. These therapies are hindered by costs, compliance and side effects. Managing drug side effects in an elderly population is difficult.

Tissue modifying procedures without device implantation have traditionally been secondary or complimentary approaches to the pharmaceuticals. These surgical procedures include trabeculectomy and laser trabuculoplasty. Trabeculectomy is very invasive surgery with considerable side effects. Scarring of the treated area is the greatest risk for failure. Antimetabolite and antineoplastic medications are often needed to augment the procedure. Other risks include infection, haemorrhaging, cataract formation, and hypotony. With hypotony, if the pressure remains too low for prolonged periods maculopathy and possible vision loss my result. Laser trabuculoplasty is more widely utilized because of its less invasive nature. Both procedures have very limited success and usually still require chronic paramedical use. All procedures which involve surgical trauma to compromised tissues must contend with the tissue's natural healing mechanism. The early positive response often renders a compromised eye at greater risk for failure. There is a shift now to improved surgical procedures as a primary treatment. An effective single procedure has the potential to reduce costs and eliminate compliance issues. Most devices available as treatments are focused on by-passing or bridging elements of the drainage pathway. The development and improvement of glaucoma shunts or stents remains a very active field of investigation. The ultimate goal is to have a single surgical procedure as a first line treatment. There are various shunt designs that continue to evolve. The basic principle is to bypass the resistance of the trabecular meshwork and allow flow of the aqueous humor directly into the Schlemm's canal. If the shunt can remain clear, the pressure in the anterior chamber will remain equalized with the pressure in Schlemm's canal. From there on, the uveoscleral outflow pathway remains intact to modulate IOP. The surgical implantation of such a small stent requires the extreme precision of a skilled surgeon. It is also difficult to be confident that the stent has penetrated the tissues as required to be effective. The lumen of the stent must remain open. The risk of scarring and blockage will always be of concern for patency.

All glaucoma treatments and variations of treatments have notable disadvantages and limited success. Medication has significant side effects and surgery results in tissue trauma. In both cases, the cost of treatment is high. The average direct cost of glaucoma treatment ranges from $623 per year for patients in the earliest stages and in excess of $2,500 a year for end stages of the disease. The annual total costs for glaucoma are approaching $3 billion in the U.S. economy alone. Procedural short term benefits can often result in additional costs associated with failure and complications. A true treatment for glaucoma is a common goal. The drainage systems of the eye may be best left intact if it is possible to provide assistance to circumvent the degenerative process. Trauma and scarring will inevitably compound the regenerative process. Implantation of a device to provide structural support offers promise. It may be possible to cure glaucoma through proactive prevention. Stem cell activity and cellular regeneration in the trabecular meshwork also are likely involved. A device to stimulate the responsible stem cells along with structural support could provide the eye with all that is necessary to prevent the manifestation of glaucoma.

Fuchs' Corneal Dystrophy is a group of degenerative diseases of the corneal endothelium. The endothelium is a monolayer of specialized, flattened, mitochondria-rich cells that line the internal surface of the cornea. Fuchs' dystrophy is clinically observed as an accumulation of focal outgrowths called guttae which are a thickening of the Descemet's membrane. This results in corneal edema leading to decreased vision and potentially vision loss. It is estimated that 5-10% of the population over 50 years old have clinically significant manifestation of the disease. The underlying cause is a deficiency of corneal endothelial cells. The density of endothelial cells on the posterior surface of the corneal predictably decline with aging. There has been significant research and discovery in the genetics of Fuchs' variants. There are early and late onset variations, and women tend to be more affected at an early stage. The common link to all is the decline in endothelial cell density. Evaluation of the endothelium by specular microscopy can demonstrate classic changes of Fuchs' endothelial dystrophy. With the background of the invention in mind, discussion will focus on the corneal endothelium and its role. The principal physiological function of the corneal endothelium is to allow nutrients from the aqueous humor to diffuse into the superficial layers of the cornea, while at the same time actively pumping water out of the cornea back into the anterior chamber. Thus, the corneal endothelium effectively keeps the cornea from becoming edematous and losing clarity. Treatment options vary depending on severity of symptoms and state of disease progression. Early treatments are targeted at reducing the edema. These treatments include topical dehydrating agents, warm air to increase evaporation, lowering IOP, and topical nonsteroidal anti-inflammatory drugs. Treatment is necessary until it is not possible to preserve good vision; at that point keratoplasty is necessary. Penetrating keratoplasty (PK) has been the standard for treatment of Fuchs' endothelial dystrophy. PK involves replacement of the full corneal thickness with donor tissue, even though only the endothelial layer is defective. In recent years, major advances in this field have made replacement of only the endothelial layer possible, without disturbing normal anterior structures of cornea using endothelial keratoplasty. Both are effective procedures, but often have complications and limited duration of effectiveness. Approximately 10% of those identified with the dystrophy will need keratoplasty. The purpose of transplantation is to increase endothelial cell density and thus restore function. As a result, a procedure that allows the eye to regenerate its own endothelial cells may be an effective treatment option. Recently the stem cells responsible for this have been located in the posterior limbus. At this junction between the cornea and sclera, there is an area known as the transition zone where stem cells believed to be responsible for endothelial and trabecular meshwork cells reside. Schwalbe's Line demarks part of the transition zone. The stem cells have been observed to be stimulated after laser trabuculoplasty for glaucoma treatment. Stem cells are known to be activated by trauma. In these cases, the stimulation can be beneficial or detrimental if over stimulated. Mechanical forces are also known to trigger stem cell differentiation. The mechanical stimulation model may be very significant with respect to corneal endothelium regeneration. The link to a decline in endothelial cell density and age may very well be correlated to a decline in accommodative ability. By the age of 45, approximately half of our endothelial cells and most of the ability to accommodate have been lost. A child has potentially ten times more accommodative ability than necessary. Such excessive power to focus would translate into significant forces induced by the ciliary muscles and accommodative apparatus. The transition zone where the stem cells are located absorbs some of these forces. It would be logical to expect certain level of cellular activity to result. Implantation of a device to induce mechanical forces to the transition zone would have the potential to stimulate stem cells. The device will need to provide an appropriate amount of stimulation by means of variable forces and contact area with the transition zone. If a healthy population of endothelial cells can be maintained, Fuchs' dystrophy should not manifest. The underlying genetic predisposition will still exist, but induced mechanical stimulation has the potential to prevent the disease symptoms from manifesting.

Retinal Detachments are generally categorized into idiopathic, traumatic, advanced diabetic, and inflammatory disorders. The majority of disorders fall into the idiopathic classification. This grouping of spontaneous retinal detachments dramatically increases after the age of 40 and peaks at about the age of 60. The bulk of these idiopathic detachments are vitreoretinal in origin. The vitreous humor changes in consistency with aging. Its boundaries shrink away from the retina. This separation is known as a posterior vitreous detachment (PVD). As the vitreous separates, it can pull the retina with it in areas of excessive adhesion. The incidence of retinal tears resulting from a PVD varies on average between 5% and 15%, depending on the presentation. The process of the PVD can be asymptomatic or symptomatic with photopsia. Flashes or sparks of light in the absence of true light are indicative of tension at retinal adhesions and present with greater risk. The symptoms usually subside once the process resolves. Floaters may remain after the process is complete. In the event that the adhesions does not release, a retinal detachment is likely to occur. Retinal detachments of this etiology have a particularly strong correlation with the decline in accommodative ability. It is known that the ciliary body remains active even with lack of any sustainable accommodation. The feedback mechanisms to accommodate also remains, but the cortical stimulation to accommodate is met with a lack of response that ultimately can produce an over active muscular response of the accommodative apparatus. The vitreous body and the zonular attachments have a significant role in the apparatus. There is debate over what is responsible for the ability to accommodate. The exact combination of actions and reactions is not important for the discussion of retinal detachment associated with PVD's. What is significant is the balance of forces. When the ciliary body contracts it relaxes the circumferential lenticular zonules. These include the equatorial, anterior, and posterior zonular limbs The area of traction exists along the anterior hyaloid of the vitreous body. There are hyaloid zonules that anchor here and ultimately transfer forces to retinal adhesions. The dramatic increase in retinal detachment must have some relation to the actions of the complex accommodative mechanism. When the eye has adequate accommodative control, there is a balance between ciliary contraction and relaxation. The accommodative mechanism would predominately be in a relaxed state, when viewing beyond a few feet. Effectively this state puts tension on the lenticular zonule complex, pulling the lens back and relieving tension on the retinal attachments. The opposite is true of the response to near focus. The ciliary body contracts releasing tension on the lenticular zonule attachments. The vitreous body and its gelatinous characteristics push the lens forward to accommodate. The forward movement is retained by tension transferred around the anterior hyaloid and retinal attachments. With presbyopia the concern is how the feedback mechanism responds to a lack of focus. The action and reaction do not balance and cause instability. The ciliary body easily can go into spasm under these circumstances. These spasms can clinically present as ocular pain. The ciliary muscle may very well become stronger as accommodative ability diminishes with aging. The retinal adhesion will be put under significant traction resulting in the inevitable PVD and risk of retinal detachment. The relationship is complex and it is difficult to isolate the components of the accommodative mechanism. Other tissue related changes with aging must also be factors.

Retinal tears and detachments are treated by a variety of procedures. Success of treatment is high if the detachment is treated in a timely manner. When tears are seen clinically there are generally two approaches, laser photocoagulation and cryopexy. Both methods essentially scar the tissue around the tear to stabilize it. Retinal detachments have more involved surgical treatments. Pneumatic retinopexy is the least invasive. The procedure involves injecting a gas bubble in the eye to float the retinal back in place where it can reattach. Photocoagulation or cryopexy are then used to stabilize any holes or tears. Scleral buckling surgery is another surgical procedure. The surgeon places a piece of silicone sponge, rubber, or semi-hard plastic on the outer layer of the eye and sews it in place. This relieves traction on the retina, preventing tears from proceeding to detachments, by supporting the retina. The most invasive treatment is a vitrectomy. This procedure involves removal of the vitreous body from the eye. Vitrectomy gives the surgeon better access to the retina to repair holes and close large tears.

A procedure that could restore a functional amount of accommodation could reduce retinal traction by stabilizing contraction of the ciliary muscles. The feedback would be restored and the accommodative system would predominately be in a state that relieves tension on the vitreous base and retina. To achieve this reduction in retinal traction, the anterior displacement of the whole system must be returned to a more posterior position. This repositioning could be achieved through careful calculated sizing and implantation of a device to provide structural support and targeted appositional forces.

Refractive Error Correction encompasses a variety of approaches to achieve clear vision. All eyes have a need for visual assistance by optical or surgical procedures during a life time. Emmetropia is the most common presentation. This is a state of vision when one requires no optical aids to see clearly when distant viewing. These individuals have no need for correction until presbyopia sets in at mid life. This loss of accommodative ability is true of all eyes regardless of distance refractive status. The non emmetropic eyes can be divided into myopia or hyperopia, respectively nearsighted or farsighted eyes. Astigmatism is generally present in variable amounts. This represents an unequal curvature of the cornea or internal lens of the eye. There are infinite variations in refractive error and many treatment options available. The most common treatments include spectacles and contact lenses. Essentially all refractive errors can be treated by variations of these solutions. There are many other refractive modification procedures available. Mostly these treatments are elective lifestyle procedures, but in some cases medically necessary. Cataract surgery is an example of necessary surgery. Cataract extraction is the most common surgical procedure in the United States. There are two types of cataract surgery commonly employed today. Standard extracapsular cataract extraction involves removal of the lens in one piece along with the front portion of the lens capsule. This procedure is still utilized, but in limited circumstances due to the larger more invasive incision needed. Phacoemulsification small incision cataract surgery is essentially the standard of care. The surgery utilizes ultra sound energy to fragment the lens so it can be evacuated through the small incision port. The technique employs a foldable posterior chamber interocular lens (PCIOL) to facilitate transplantation through the small incision. The PCIOL is positioned in the remaining lens capsule structure and centrally positioned by flexible haptics. This small incision technique has generally replaced other procedures. It is noted that there are a wide variety of PCIOL's available in various designs and materials. Surgeons have significant surgical liberties in the cataract extraction field. Foldable anterior chamber interocular lenses (ACIOL) have recently been developed. These lenses are employed by the same small incision technique. They are placed in the anterior chamber and positioned by flexible haptics resting in the anterior chamber angle. ACIOL's are generally designed to be used in phakic eyes as they are positioned in the chamber anterior to the lens. This is usually an elective procedure to correct high or difficult prescriptions. The procedure is resorted to when other refractive devices or surgical options are not possible or have limited potential.

The market for elective refractive surgery is well established. Refractive surgery without device implantation includes: Radial Keratotomy (RK), Astigmatic Keratotomy (AK), Photo-Refractive Keratectomy (PRK) and Laser Assisted In-Situ Keratomileusis (LASIK). RK and AK involve carefully placed superficial incisions into the corneal stroma in a radial fashion. These procedures are not performed anymore, and are predecessors that led to PRK and LASIK. The utilization of lasers with PRK and LASIK has much greater control and predictable outcomes. Modern PRK and LASIK are considered elective procedures. They can correct most naturally occurring refractive errors. These are not truly reversible techniques because tissue is removed with the laser.

The implantation of interocular lenses accounts for nearly all of the devices implanted to correct refractive errors. The laser surgery techniques dominate the tissue altering procedures by re-shaping the cornea. Intra-stromal corneal rings are an alternative option for low levels of myopia and astigmatism. Small incisions in the corneal stroma are made. Two crescents or semi-circular shaped ring segments are implanted on opposing sides away from the central cornea. The embedding of the rings in the cornea has the effect of flattening the cornea and changing the refraction. Intacs are the FDA approved device for this procedure. They are made of a relatively rigid material, Poly(methylmethacrylate) (PMMA). Intacs have not gained significant market share despite being marketed as a reversible procedure. Presently they are often used for the treatment of Keratoconus. Their semi-rigid structure offers support to a structurally failing cornea. There is extensive data from photorefractive surgery and cornea curvature altering proceeds. The cornea has an average refractive power of 45 diopters. This high power along with 18 diopters from the natural lens is required to focus light to produce images at the 24 mm axial length of the eye. The majority of naturally occurring refractive errors are within a prescription of one diopter. This is a very small amount with respect to the total power of the system. A device with the ability to internally expand along the corneal base would flatten corneal curvature resulting in decreased myopia. The cornea only requires a flattening of 75 microns to achieve a one diopter decrease in myopia. Achieving such a flattening of the cornea would only require an increase in diameter of 60 microns at the corneal base.

The loss of accommodative ability remains one of great interest within the field of refractive correction. The ability to change focus provides the optical system control and an advantage over any static approach. The development of a device to rejuvenate the natural ineffective aged system is being actively perused. The advantages of such a system could be more significant than the visual control and clarity. Stability of the accommodative musculature has the ability to relieve the retinal tension by returning the system to equilibrium. Present techniques and procedures under investigation to restore accommodation are either external or internal to the posterior chamber. Externally there are techniques that suggest the suturing of bands around the eye to increase the diameter and provide a more rigid external base for the ciliary muscles internally. The concept is to reduce flaccidity of the zonular complex by external expansion to enable some reaction to the accommodative actions of the ciliary muscles.

However, the eye is dynamic and changes in refractive status do have predictable patterns as well changes that cannot be anticipated. In theory, the eye cannot be static until it is aphakic after cataract surgery. At this stage there is no effective accommodation. The cortical connections and accommodative musculature still remain, but no lens remains to facilitate a response. Developing a way of utilizing the cortical and muscular system to facilitate accommodation will be of great benefit. An artificial lens is required to achieve this. Focusing PCIOL's are in development and are already available. The lens is implanted in the posterior chamber replacing the natural lens. The concept is to have a lens with shape changing characteristics to harness the movement of the ciliary muscle during accommodative stimulation. These lenses will continue to develop, but presently have limited success. Harnessing accommodative forces in the anterior chamber would allow for the development of a shape changing lens implant in front of the iris.

SUMMARY OF THE INVENTION

A stent device implanted into the anterior chamber angle could provide various structural elements and forces to restore some accommodative ability in the phakic eye. The stent must have precise anatomical placement to achieve this. The positioning of the stent is essentially along the internal foundation of the cornea. In this position it can induce forces radiating outward and anteriorly along the posterior cornea base. The forces would translate to a re-positioning of the accommodative apparatus to a more posterior placement. In this position the eye can restore some level of accommodation. The forces applied at the corneal base can also be adjusted to manipulate corneal curvature and change refractive error.

In addition, the stent device implanted at the internal base of the cornea could translate motion if it can articulate. Embodiments of such a device would provide a base to implant the novel concept of a focusing ACIOL. The stent device, along with the additional here in claimed invention of the complimentary focusing ACIOL, has the potential to provide pseudo-accommodation. This configuration of an accommodating ACIOL will be discussed in relation to the stent device but should not be limited to the preferred embodiments to be discussed and illustrated. The concept of an accommodating ACIOL is dependent on the specific anatomical fitting of the stent device and as such is considered an extension of this invention. The stent of the present invention is configured to provide such features.

Therefore, generally provided is a surgically-implantable device for the human (or mammalian) eye that addresses or overcomes some or all of the deficiencies and drawbacks in the field of medical eye care. Preferably, provided is a surgically-implantable device for the human (or mammalian) eye that facilitates the restoration of the architecture of the anterior chamber angle and underlying accommodative apparatus. Preferably, provided is a surgically-implantable device for the human (or mammalian) eye that provides the eye with ability to restore, regenerate and rejuvenate various elements of normal function. Preferably, provided is a surgically-implantable device for the human (or mammalian) eye that addresses the clinical need for a faster, safer and more cost effective method to treat diseases and degenerative conditions of the eye.

The anatomical area of implantation is very specific, but within the anatomy there will be various embodiments of devices. The description of preferred embodiments of this invention is not limited to variations in design, materials, manufacturing and procedures relating to implantation of the invention. Any embodiment of this device will involve minimally invasive small incision by clear cornea, modified clear cornea or scleral tunnel implantation techniques. Preferred embodiments of this device would be removable and thus enable reversal of failed procedures.

The device may be specifically fit according to the involved anatomy and patient specific sizing with respect to this anatomy. Recent refinements and advances in imaging technology are now allowing for very accurate clinically available equipment. The introduction of time domain anterior segment optical coherence tomography (AS-OCT) technology allows for in vivo, cross-sectional tissue imaging. This provides diagnostic and management capabilities that is far superior then before. Prior to the introduction of this technology in 2006, the only way to obtain cross-sectional images of the anterior segment was with histological sectioning The importance of this technology is apparent when applying the specific anatomical placement of the potential embodiments of the device.

In a preferred and non-limiting embodiment, an ocular stent for insertion in an anterior chamber of an eye includes an annular body. The body includes: an anterior portion configured to contact a surface of a transition zone between a trabecular meshwork and a corneal endothelium of the eye; a posterior portion configured to contact a peripheral iris of the eye; and a central portion connecting the anterior portion and the posterior portion of the body.

In certain embodiments, the anterior limits of the device may encroach on and make contact with the adjacent trabecular meshwork and corneal endothelium. The posterior portion of the device will be configured to be in contact with a portion of the surface of the peripheral iris. The peripheral limits of the posterior contact may extend around the anterior chamber irideocorneal angle to cross the anterior chamber exposure of the ciliary body up to or beyond the scleral spur to encroach on the trabecular meshwork. The central range of the posterior contact along the iris will be sufficient to support the range of the ciliary body structure posterior to the iris. The anterior and peripheral portions of the device will have structural connection with configuration to maintain the device out of contact with the majority (or other proportion) of the surface of the trabecular meshwork.

Additionally, certain embodiments of this invention have a grouping of objectives that are inherent to the action of mechanically restoring anatomical architecture of the aging eye. Implantation of the device will inevitably have multiple actions regardless of the desired action. By design, the device cannot single out any one objective without including the other complimentary objectives. As such the device can be seen to have the primary objective of reversing the natural aging processes with respect to certain aspects of the eye.

In accordance with a further preferred and non-limiting embodiment, an ocular stent for insertion in an anterior chamber of an eye is provided. The stent includes: at least one annular cord; a plurality of anterior arms extending from the cord in a first direction; and a plurality of posterior arms extending from the cord in a second direction, the second direction being different than the first direction. The stent is configured to be receivable within an irideocorneal angle of the anterior chamber of the eye. Additionally, the anterior arms and the posterior arms together are configured to form an articulating joint.

The above-describe exemplary embodiments of the invention are provided for treatment of eye conditions related to aging. One aspect of the invention relates to a medical device system for treating the tissues of the trabecular meshwork. The trabecular meshwork and the juxtacanilicular tissue collectively are responsible for the resistance to the out flow of the aqueous humor. The trabecular meshwork is thus a logical target for tissue rejuvenation and stimulation for the treatment of glaucoma. The various possible embodiments of the device all apply appositional forces anterior and posterior to the trabecular meshwork. Preferred embodiments may have partial contact with the trabecular meshwork. Significant contact with the anterior portion of the trabecular meshwork may produce increased stem cell activity. As such, centering the anterior portion of the device at an anterior portion of the trabecular network may provide improved results. Despite any contact, the device will effectively span and open the structure to enhance flow of the aqueous. Since there is no true treatment, control of the disease is the goal. Lowering IOP by 20% relative to pre-treatment levels is a general rule to measure initial success.

Another aspect of the invention relates to stem cell activation by appositional stimulation to the posterior limbus transition zone. There is evidence of stem cells for the corneal endothelium as well as stem cells for the trabecular meshwork residing there. Successful stimulation has regenerative potential for Fuchs' corneal dystrophy and glaucoma respectively. Regeneration of trabecular meshwork tissues would be very complimentary to the aforementioned structural aspect of the device to increase outflow. Stimulation of the endothelial stem cells offers promise as a potential treatment or prophylactic measure to circumvent normal endothelial cellular loss with aging. Mechanical stimulation of stem cells is well known in various tissues of the body. Regular physical stimulation of tissues is often needed to maintain the regenerative processes. The internal limbal transition zone of the cornea does not have the same mechanical stimulation as the external limbal area responsible for epithelial regeneration. There is continual direct mechanical interaction with external eye and perpetual regeneration is required to sustain healthy tissues of the external eye. The internal transition zone must have internal mechanical stimulation by translation of accommodative energy. A child's excessive accommodative ability can translate into forces greater than ten times that of the middle aged adult. Embodiments of this device will have the ability to produce variable amounts of appositional forces on the transition zone. Although different in presentation than accommodative forces, it is hypothesized that such appositional force will result in favorable stem cell activity. Such activity can be easily measured as it relates to endothelial cell density. Evaluation of the endothelium by specular microscopy is a non-invasive way to achieve this.

Some other aspects of the invention relate to repositioning and stabilization of the accommodative apparatus. The posterior contact of the various embodiments is essential to the overall function of the invention. The anatomical placement of this contact is such to transfer an adequate amount of force through the iris base to result in a posterior repositioning of the ciliary body. This repositioning of the accommodative apparatus will be restorative to some accommodative function. The ability to restore focusing ability is a very desirable aspect of the device embodiments. Calculations and adjustments will be patient specific to achieve the desired results. Loss of accommodation is not classified as a disease, but rather considered an inconvenient result of aging. It is a degenerative condition that does relate to the manifestation of disease processes. Implantation of an embodiment of this device for the purposes of restoring accommodation or changing refractive status will also have benefit(s) of the additional aspects of the device.

Another attribute of the device relating to repositioning of the accommodative apparatus is retinal stabilization. The physical posterior shifting of the ciliary body will relieve excessive tension translated to retinal attachments linked to the accommodative apparatus. Restoring accommodative control is also a significant part of reducing retinal detachment. Accommodative control will allow for stable control of the ciliary muscle and reduce or prevent ineffective unnecessary contractions. The various embodiments will be able to be sized to achieve the desired effect and reduce the risks associated with retinal detachments of this etiology.

Embodiments of the invention can be designed to position an AIOL. The specially designed lens can be retained in the base structure of the invention. The implantation of such a lens would be indicated with cataract extraction, but variation could be employed with a phakic eye as well. The circumferential designs of the invention, in its articulating foams, will allow for the opportunity to develop a lens capable of changing its radius of curvature and position in relation to natural accommodative stimulation and muscular response. The ciliary body muscle induces forces during accommodation that can allow the articulating embodiment to induce small amounts of movement. The movement would radiate inward upon contraction of the ciliary body with accommodative stimulation. Accommodative feedback and ciliary muscle action are still active even in the aphakic eye. There is no response without the natural lens, or a PCIOL that is static. Implantation of a lens that can tie into the feedback mechanisms would return the control of focus. There is very significant prior art with respect to implantable lenses. This design concept to work with embodiments of the invention is a new concept that can utilize acrylic and silicon-based materials. The design of this lens must have sufficient ability to change curvature with small amounts of movement allowing a functional accommodative range. It will require a PCIOL of opposing power to complete the optical system. Calculations based on pairing of lenses can produce accommodative responses in excess of that required under normal visual demands. Preferred embodiments of this complimentary device are to be considered an extension of the original invention, and not to be limited in design, materials or manufacturing process.

A variety of biocompatible materials can be employed to manufacture the embodiments of the device and components of this invention. The device may utilize such a variety of materials, many of which have ongoing proven bio-compatibility in excess of 25 years. All embodiments of the device(s) are to be removable and replaceable. The device(s) will be visible by mean of non-invasive visual and imaging assessment. The following materials are examples but not to be considered limiting for the design and manufacturing of the device(s) and possible components of the invention. There are a variety of proven biocompatible materials used in various ocular implants. The original interocular lenses were made from Polymethylmethacrylate (PMMA) and were not foldable. Presently, the most common ocular implants are the posterior chamber interocular lens (PCIOL). These are primarily made of silicone or acrylic and often have PMMA components. The material of choice for single piece embodiments must be bio-compatible, semi rigid, foldable and have a constant memory of shape. A clear material would be cosmetically favorable since the ring will be partially visible. It may also be possible to color match or enhance the iris color. There is significant debate over whether hydrophilic or hydrophobic materials or surface treatments are superior.

Some proven PCIOL's utilize both properties. Potential materials may include: Hydrophobic Acrylic, Hydrophilic Acrylic, Acrylic Polymer, Silicone, Poly(styrene-block-isobutylene-block-styrene) SIBS, Silicon Elastomer (Biosil), and Heparin Surface Modified Acrylics. The annular design of the device can allow for very soft and pliable materials to induce sufficient forces. The involved soft tissues will require delicate and controlled contact. The multi-piece embodiments can utilize a wider range of materials since the individual components do not require the same flexibility as those to be utilized in the single-piece embodiments. A proven material, such as PMMA, can be utilized. It has rigid properties, is extrudable and stable for laser cutting or lathe turning. Other methods of manufacture can include: molding techniques, vacuum forming, and solvent casting. Particular methods of manufacture have not been disclosed. It is understood that a variety of manufacturing methods do exist with substantial prior art in the field of ocular implants. One or multiple methods of manufacture may be employed in the manufacture of single or multiple components of the possible embodiments of this invention. It may also be useful to coat components of this device to enhance its functional properties or biocompatibility. It may also be useful to coat the device with therapeutic agents or implant a complimentary device containing therapeutic agents.

According to a further aspect of the invention, a method of stabilizing the irideocorneal angle of an anterior chamber of an eye demarked by the cornea and iris is provided. The method includes the step of inserting a stent into the anterior chamber, such that the stent is in contact with soft tissue of the anterior chamber. Following insertion of the stent, pressure is applied, simultaneously, in an anterior direction to a surface of a transition zone between an anterior limit of a trabecular meshwork and a posterior limit of a corneal endothelium of the eye with an anterior portion of the stent, and in a posterior direction to a surface of the peripheral iris of the eye with a posterior portion of the stent.

More particularly, implantation of the various possible embodiments of the device would be in accordance to the prior art of cataract surgery relating specifically to the implantation of foldable interocular lenses. The present state of lens implantation is highly developed, and those skilled in the art have a variety of choices as to their preferences in materials and tools. Virtually all implanted ocular lenses are foldable, allowing for small, minimally-invasive, sutureless incisions. Smaller incisions that allow quicker recovery, better wound strength and increased surgical control, result in lower complication rates and better outcomes. Diamond spade knives are used to make a 2-3 mm incision through peripheral cornea or scleral tunnel techniques. The interocular lenses are pushed through the small incision with a variety of injector devices that usually consist of a cartridge that prepares the lens by folding it and a plunger system to inject it. Those skilled in the art can utilize these established devices for purposes of implanting embodiments and components of the device. Although new tools may not be needed for purposes of implantation of the device(s), it will become apparent to those skilled in the art which available devices are best suited as techniques evolve. Refinements of the tools and techniques may lead to development of specific new tools for implantation, manipulation and removal of the various stent devices.

The embodiments of this medical device and methods are provided in accordance of the objectives to rejuvenate or restore elements of the eye. The disease processes and physiologic changes herein mentioned above are as such detrimental to function. For purposes of summarizing the invention, certain aspects, features and advantages of the invention have been described. It is herein to be understood that not all advantages of this invention may be achieved in relation to any particular embodiment of the device(s) or adjunctive components of the device(s). As such, the invention may be embodied in configurations to optimize one or various advantages. Implantation of the device may be indicated for any one advantage or combination of advantages as indicated for treatment or prophylactic intervention.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

Additional aspects and advantages of the invention will become readily apparent to those skilled in the art upon reference to the provided figures and detailed description of the preferred embodiments. The invention is not limited to any particular preferred embodiment(s) disclosed.

BRIEF DESCRIPTION OF THE DRAWINGS

Some of the advantages and features of the preferred embodiments of the invention have been summarized herein above. These embodiments along with other potential embodiments of the device will become apparent to those skilled in the art when referencing the following drawings in conjunction with the detailed descriptions as they relate to the figures.

FIG. 3 is a schematic sectional view of an eye showing anatomical detail along with in situ placement of a stent, in accordance with an aspect of the present invention;

FIG. 3A is a schematic sectional view of the eye and stent of FIG. 3 taken along section 3-3, in accordance with an aspect of the present invention;

FIG. 4A is a schematic illustration of a divided front view of a stent illustrating continuous and/or divided variations of a ring, in accordance with an aspect of the present invention;

FIG. 4B is a cross-section view of the stent of FIG. 4A taken along section 4B-4B, in accordance with an aspect of the present invention;

FIG. 4C is a partial side profile view of the stent of FIG. 4A taken along section 4C-4C and having drainage ports, in accordance with an aspect of the present invention;

FIG. 4D is a cross-section view of the stent of FIG. 4A taken along section 4D-4D, in accordance with an aspect of the present invention;

FIG. 4E is a partial side profile view of the stent of FIG. 4A taken along section 4E-4E and illustrating a beaded anterior surface, in accordance with an aspect of the present invention;

FIG. 5 is a schematic sectional view of an eye showing anatomical detail along with in situ placement of a stent, in accordance with an aspect of the present invention;

FIG. 5A is a schematic sectional detail of the eye and stent of FIG. 5 taken along section 5-5 in accordance with an aspect of the present invention;

FIG. 6A is a schematic front view of a stent illustrating a single piece non-continuous ring with a continuous tensioning O-ring in place, in accordance with an aspect of the invention;

FIG. 6B is a cross-section view of the stent of FIG. 6A taken along section 6B-6B, according to an aspect of the present invention;

FIG. 6C is a partial side profile view of the stent of FIG. 6A taken along section 6C-6C, in accordance with an aspect of the present invention;

FIG. 7 is a schematic sectional view of an eye showing anatomical detail along with in situ placement of a stent, in accordance with an aspect of the present invention;

FIG. 7A is a sectional detail of the eye and stent of FIG. 7 taken along section 7-7 in accordance with an aspect of the present invention;

DETAILED DESCRIPTION OF THE PREFERRED EMBODIMENTS

Figure 1:
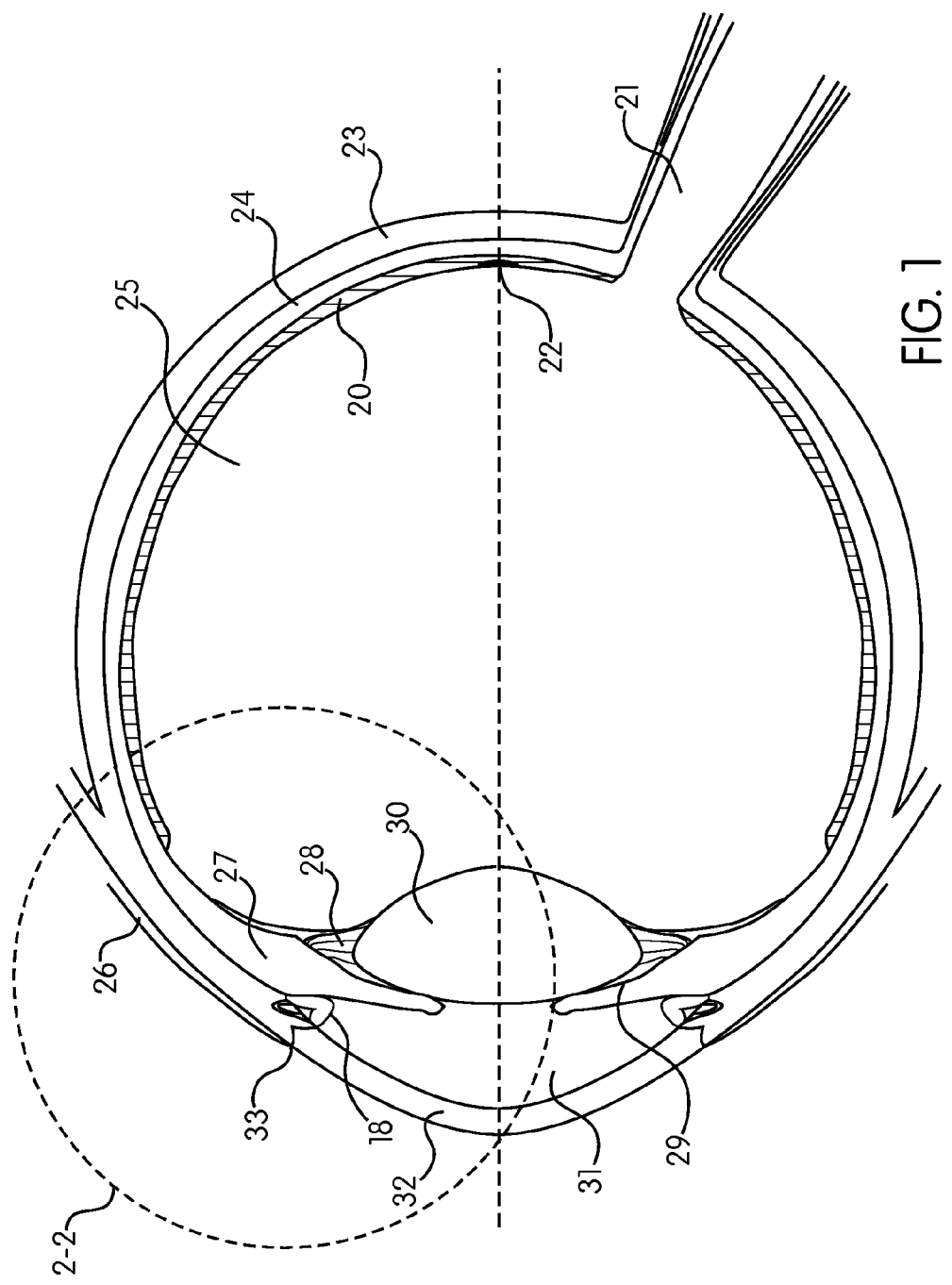
FIG. 1 is a schematic sectional view of an eye showing anatomical detail along with in situ placement of a stent, in accordance with an aspect of the present invention.

The illustrations generally show preferred embodiments of the devices used to treat predictable structural ocular aging changes of the anterior segment of the human eye. While the descriptions present various embodiments of the device(s), it should not be interpreted in any way as limiting the invention. Furthermore, modifications, concepts and applications of the inventions embodiments are to be interpreted by those skilled in the art as being encompassed, but not limited to the illustrations and descriptions herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention. Further, for purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. For the purpose of facilitating understanding of the invention, the accompanying drawings and description illustrate preferred embodiments thereof, from which the invention, various embodiments of its structures, construction and method of operation, and many advantages may be understood and appreciated.

A sectional view of an eye is illustrated in FIG. 1. The ocular stent 18 in this anatomical placement represents certain preferred and non-limiting embodiments. It is positioned in the anterior chamber of the eye. This chamber is bound by the cornea 32 anteriorly and the iris 29 posteriorly. Aqueous humor 31 fills and circulates through this chamber. The cornea 32 is a clear collagenous tissue responsible for most of the focusing ability of the eye. It transitions into the white collagenous tissue of the sclera 23 along the limbus 33. The lens 30 is suspended by the zonular complex 28. The zonules 28 are ligamentous having their muscular attachments to the ciliary body 27 and opposing attachment into the equatorial region of the lens 30. The ciliary body 27 is the muscular component of the accommodative complex. Along with the ciliary body 27 and iris 29, the choroid 24 forms the uveal tract. The choroid 24 is the highly vascular layer which underlies the retina 20. The retina 20 is centrally bound by the vitreous body, which is filled with vitreous humor 25. This central body makes up the bulk of the volume of the eye. It maintains the eye's shape and plays a role in accommodation. The central visual axis intersects the retina 20 at the fovea 22 of the macular region. This region is the most visually sensitive and innervated area of the retina 20. All innervations and vascularisation of the eye is connected to the brain via the optic nerve 21.

Figure 2:
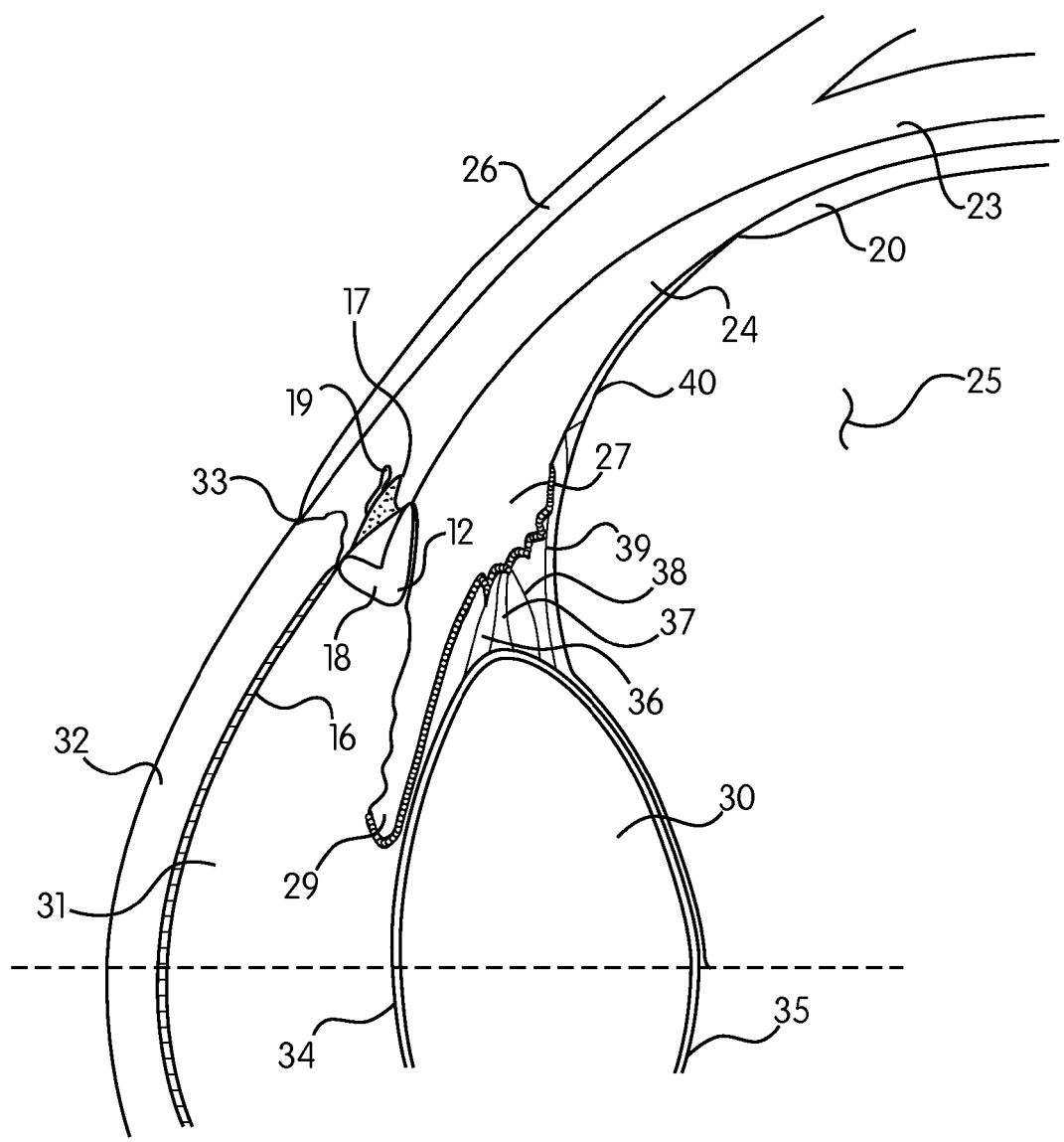
FIG. 2 is a close up sectional view of FIG. 1 taken along section 2-2, providing more anatomical detail of the superior anterior segment of the eye relating to the stent, in accordance with an aspect of the present invention.

In FIG. 2, the anterior segment of the eye is shown with additional anatomical detail around a preferred and non-limiting embodiment of the ocular stent 18. The drainage structure of the trabecular meshwork 17 and Schlemm's canal 19 are illustrated. The corneal endothelium 16 is illustrated as are the anterior 34 and posterior 35 lens capsules. The zonular attachments to the lens 30 and ciliary body 27 are divided into the anterior zonules 36, equatorial zonules 37, posterior zonules 38 and hyaloid zonules 39. The anterior hyaloid vitreous membrane 40 is the anterior boundary of the vitreous humor 25.

FIG. 3 is a detailed illustration of a preferred and non-limiting embodiment the ocular stent 18 in relation to adjacent anatomy. The ocular stent 18 is implanted in the peripheral irideocorneal angle 44 of the anterior chamber, having an anterior portion configured to be centered on and in contact with the surface of the transition zone 42 between the anterior limits of the trabecular meshwork 17 and posterior limits of the corneal endothelium 16 or posterior aspect of the limbus 41. The anterior limits of the ocular stent 18 may encroach on and make contact with the adjacent trabecular meshwork 17 and corneal endothelium 16. The posterior portion of the ocular stent 18 will be configured to be in contact with a portion of the surface of the peripheral iris 29. The peripheral limits of the posterior contact may extend around the anterior chamber irideocorneal angle 44 to cross the anterior chamber exposure of the ciliary body 27 up to or beyond the scleral spur 43 to encroach on the trabecular meshwork 17. The central range of the posterior contact along the iris 29 will be sufficient to effectively support the ciliary body 27 structure posterior to the iris 29. The ocular stent 18 may be formed with a boomerang shaped radial cross section. In that case, the anterior portion and the posterior portion of the ocular stent meet at a central portion 12. As will be appreciated by those having skill in the art, the central portion 12 may be integrally formed with the anterior and posterior portions of the body. Alternatively, the central portion 12 may be a joint, such as an articulating joint.

As will be appreciated by one having ordinary skill in the art, the stent 18 may be able to reposition and retain the position of the ciliary body 27. For example, in the embodiment depicted in FIG. 3, the ocular stent 18 is positioned in the anatomy of the eye to enable favourable function. The ocular stent 18 spans the filtering structure of the trabecular meshwork 17 expanding and opening its porous structure. This structurally supported configuration of the drainage anatomy will decrease IOP and promote rejuvenation of the tissues. In certain embodiments, the ocular stent 18 is composed of a biocompatible material that has structurally stable properties. The integrity of the anatomical organization will remain since the properties of the ocular stent 18 are required to be stable. These stable properties also will allow for consistent and accurate contact with the transition zone 42. This is required to induce appropriate forces at this area of stem cell activity. The appositional stimulation of stem cells here can impact regeneration of corneal endothelial cells 16 and cells pertaining to the trabecular meshwork 17. The posterior aspect of the ocular stent 18 is configured to assist in positioning of the trabecular meshwork 17 and transition zone 42. This posterior contact along the iris 29 base translates forces required to reposition the ciliary body 27 and variable forces from muscular action in the ciliary body 27 to the transition zone 42. The posterior repositioning shifts the accommodative structure posteriorly which in turn requires the structures to expand circumferentially. This expansion will translate into a tightening of the posterior 38, equatorial 37, and anterior 36 zonules. The return of tension to these zonules will result in some degree of accommodative function. The return of function will stabilize muscular action by means of effective feedback and control of the ciliary body 27. This is important as it relates to the hyaloid zonules 39. The posterior movement of the ciliary body 27 will relieve excessive tension on the hyaloid zonules 39. This combined with returned control of the accommodative musculature will relieve excessive tension being transferred to the hyaloid retinal connections and thus reduce the risk of retinal detachment. The stent 18 requires very specific sizing and anatomical placement. It will be possible to adjust the sizing to induce forces to enable some manipulation of refractive error. More specifically, the ocular stent 18 is positioned at the base of the cornea 32. This area of circumferential placement is the foundation of the cornea and as such the structural base of the cornea 32.

A divided front view of a preferred and non-limiting embodiment of the ocular stent 18 is shown in FIGS. 4A-4E, for purposes of illustrating various embodiments of the stent 18. FIG. 4A illustrates a half section of a continuous variation of the ocular stent 18 having a communication structure, such as ports 14. As used herein, a "communication structure" refers to a structure such as a port, tube, opening, or through hole extending through the body of the stent 18 for permitting fluid to pass therethrough. The ports 14 equalize fluid pressures across the ocular stent 18. Six ports 14 are illustrated to convey the concept. The size and number of ports 14 can be varied to achieve a desired result. A single port 14 could be adequate to provide sufficient flow, but continued patency would be a concern so multiple ports 14 may be utilized. The ports 14 have the potential to reduce or virtually eliminate pigment dispersion into the trabecular meshwork 17. A superior placement of the ports 14 reduces pigment transfer allowing free pigment to settle inferiorly blocked by the ocular stent 18 from passing into the drainage structures. FIG. 4A illustrates a half section of a non-continuous variation of the ocular stent 18 having a beaded or textured anterior surface 15. The ocular stent can be segmented in either variation but is only illustrated in FIG. 4A. Having a small segment removed creates an internal snap ring design. This variation in design would allow for greater variability in fitting the ocular stent 18. The tensile modulus of the ocular stent 18 would allow for some variability in diameter and induced forces from a particular size. The removed segment will also provide direct access to the structures of the anterior chamber angle. It would be possible to implant a stent that penetrates the trabecular meshwork 17 to provide direct flow of the aqueous humor 31 to Schlemm's canal 19. The non-segmented variation would have virtually no variability and require precise sizing. The beaded or textured anterior surface 15 provides variable contact along the contact surface, allowing for equalization of fluid pressure across the ocular stent 18. This would be required in the case of a continuous ring design. The beading texture 15 also servers the purpose of providing a non-continuous surface in contact with the transition zone 42. Variations in the texture can be manipulated to achieve optimization of the appositional stem cell stimulation.

FIG. 4B is a sectional view of ocular stent 18 with the sectional view of a port indicated by the dashed lines. FIG. 4C is a partial side profile view of the ocular stent 18 as it would be viewed from inside the anterior chamber of the eye with the port openings visible. The illustrated view orientating is indicated in FIG. 4A. FIG. 4D is a sectional view of ocular stent 18 with the beading contour indicated. FIG. 4E is a partial side profile view of the ocular stent 18 as it would be viewed from inside the anterior chamber of the eye with the anterior beaded surface visible. The illustrated view orientating is indicated in FIG. 4A.

With reference to FIG. 5, a preferred and non-limiting embodiment of an ocular stent 47 is depicted. The ocular stent 47 is implanted in the peripheral irideocorneal angle 44 of the anterior chamber. The ocular stent 47 has an anterior portion configured to be centered on and in contact with the surface of the transition zone 42 between the anterior limits of the trabecular meshwork 17 and posterior limits of the corneal endothelium 16 or posterior aspect of the limbus 41. The anterior limits of the ocular stent 47 may encroach on and make contact with the adjacent trabecular meshwork 17 and corneal endothelium 16. The posterior portion of the ocular stent will be configured to be in contact with a portion of the surface of the peripheral iris 29. The peripheral limits of the posterior contact may extend around the anterior chamber irideocorneal angle 44 to contact the anterior chamber exposure of the ciliary body 27 up to or beyond the scleral spur 43 to encroach on the trabecular meshwork 17. The central range of the posterior contact along the iris 29 will be sufficient to effectively support the ciliary body 27 structure posterior to the iris 29. As in previously described embodiments, the stent 47 is configured to reposition and retain the position of the ciliary body 27. The ocular stent 47 spans the filtering structure of the trabecular meshwork 17 expanding and opening its porous structure. This structurally supported configuration of the drainage anatomy will decrease TOP and promote rejuvenation of the tissues. In certain embodiments, the ocular stent 47 is composed of biocompatible materials that are relatively soft and flexible. The ocular stent 47 is designed to incorporate an O-ring 48 to provide the structure with stability and ability to alter induced forces with respect to the anatomical arrangement of the involved structures. These stable properties also will allow for consistent and accurate contact with the transition zone 42. This is required to induce appropriate forces at this area of stem cell activity. The appositional stimulation of stem cells here can impact regeneration of corneal endothelial cells 16 and cells pertaining to the trabecular meshwork 17. The posterior aspect of the ocular stent 47 is essential to the aforementioned actions on the trabecular meshwork 17 and transition zone 42. This posterior contact along the iris base 29 translates forces required to reposition the ciliary body 27 and variable forces from muscular action in the ciliary body 27 to the transition zone 42. The posterior repositioning shifts the accommodative structure posteriorly which in turn requires the structures to expand circumferentially. This expansion will translate into a tightening of the posterior 38, equatorial 37 and anterior 36 zonules. The return of tension to these zonules will result in some degree of accommodative function. The return of function will stabilize muscular action by means of effective feedback and control of the ciliary body 27. This is important as it relates to the hyaloid zonules 39. The posterior movement of the ciliary body 27 will relieve excessive tension on the hyaloid zonules 39. This combined with returned control of the accommodative musculature will relieve excessive tension being transferred to the hyaloid retinal connections and thus reduce the risk of retinal detachment. In a preferred and non-limiting embodiment, the ocular stent 47 requires specific sizing and anatomical placement, but has significant adjustment due to the O-ring 48 component. It will be possible to adjust the sizing to induce forces to enable some manipulation of refractive error. The ocular stent 47 is positioned at the base of the cornea 32. This area of circumferential placement is the foundation of the cornea and as such the structural base of the cornea 32. The properties of the materials utilized for the ocular stent 47 and the O-ring 48 along with the amount of tensioning can be manipulated to create some movement of the O-ring 48 with accommodative stimulation. This motion can be utilized to incorporate an accommodating anterior chamber interocular lens (ACIOL).

A front view of a preferred and non-limiting embodiment of a stent is shown in FIG. 6A. FIG. 6A illustrates placement of the continuous O-ring 48 in the non-continuous variation of the collar stent 47 having an anterior aspect that is crenellated or notched. These crenellations 45 have a similar function to the function of the beaded surface 15 described previously. The crenellations 45 leave voids along the contact surface, allowing for aqueous flow across the ocular stent 47. The aqueous pressure does not depend on these crenellations 45 to equalize pressure. The void section of the ocular stent 47 would provide sufficient flow on its own. The crenellations 45 of the ocular stent 47 also serve the purpose of creating a non-continuous surface in contact with the transition zone 42. Variations in the texture can be manipulated to achieve optimization of the appositional stimulation of stem cells. It would be possible to produce non-crenellated variations. Such variations would work similar to the ported version of the previously described embodiments of the stent 47. In this case the void section of the ocular stent 47 is oriented up to minimize transfer of free pigment and debris. This orientation is recommended for implementations including, but not limited to, pigmentary glaucoma, pigment dispersion syndrome, and pseudoexfoliative glaucoma.

FIG. 6B is a sectional view of the ocular stent 47 with a sectional view of the O-ring 48 in position. The ocular stent 47 is designed to allow for some translation of movement induced by accommodative forces. FIG. 6C is a partial side profile view of the ocular stent 47 as it would be viewed from inside the anterior chamber of the eye with the O-ring 48 and crenellations 45 visible. The illustrated view orientating is indicated in FIG. 6A. Parts of the trabecular meshwork 17 anatomy will be visible through the crenellations 45.

FIG. 7 is a detailed illustration of the invention showing a preferred and non-limiting embodiment of an ocular stent 47 in relation to adjacent anatomy. The stent 47 is assembled from multiple pieces of three components: anterior arms 50, posterior arms 51 and annular cords, such as beading lines 52 (shown in FIG. 8C). The arms 50, 51 connect at a joint 49, such as an articulating joint. The assembled components collectively create an articulating base. An O-ring 48 is positioned within the implanted articulating base. The stent 47 is implanted in the peripheral irideocorneal angle 44 of the anterior chamber, such that the anterior aspect of the anterior aim 50 is designed to be centered on and in contact with the surface of the transition zone 42 between the anterior limits of the trabecular meshwork 17 and posterior limits of the corneal endothelium 16 or posterior aspect of the limbus 41. The anterior limits of the ocular stent 47 may encroach on and make contact with the adjacent trabecular meshwork 17 and corneal endothelium 16. The peripheral portion of the anterior arm 50 and peripheral portion of the posterior arm 51 are designed to be connected. This connection area extends around the anterior chamber irideocorneal angle 44 to contact the anterior chamber exposure of the ciliary body 27 up to or beyond the scleral spur 43 to encroach on the trabecular meshwork 17. The posterior arm 51 is configured to be in contact with a portion of the surface of the peripheral iris 29. The central range of the posterior contact along the iris 29 will be sufficient to effectively support the ciliary body 27 structure posterior to the iris 29. The stent 47 is configured to reposition and retain the position of the ciliary body 27. As shown in FIG. 7A, the stent 47 is well positioned anatomy to enable favourable function. The anterior arm 50 spans the filtering structure of the trabecular meshwork 17 expanding and opening its porous structure. This structurally supported configuration of the drainage anatomy will decrease IOP and promote rejuvenation of the tissues. The anterior 50 and posterior 51 arms of the ocular stent are to be composed of a biocompatible material that is relatively rigid. Polymethylmethacrylate (PMMA) is a suitable material; however, the ocular stent 47 components are not limited to PMMA. The material may have shape memory characteristics. As used herein, "shape memory" refers to a material which returns to an initial shape when biasing forces are removed therefrom. Shape memory may also refer to a material which returns to an initial shape as a result of a triggering event such as when the material is heated to a specific predetermined temperature. The incorporated O-ring 48 provides the ability to alter induced forces with respect to the anatomical arrangement of the involved structures. The combination of components produces a stable structure able to articulate at the irideocorneal angle 44. The relatively stable properties also allow for consistent and accurate contact of the anterior arm 50 with the transition zone 42. This contact is required to induce appropriate forces at this area of stem cell activity. The appositional stimulation of stem cells here can impact regeneration of corneal endothelial cells 16 and cells pertaining to the trabecular meshwork 17. The anterior arm 50 of the ocular stent is essential to the aforementioned actions on the trabecular meshwork 17 and transition zone 42. This posterior contact along the iris base 29 translates forces required to reposition the ciliary body 27 and variable forces from muscular action in the ciliary body 27 to the transition zone 42. The posterior repositioning shifts the accommodative structure posteriorly which in turn requires the structures to expand circumferentially. This expansion translates into a tightening of the posterior 38, equatorial 37, and anterior 36 zonules. The return of tension to these zonules results in some degree of accommodative function. The return of function will stabilize muscular action by means of effective feedback and control of the ciliary body 27. This is important as it relates to the hyaloid zonules 39. The posterior movement of the ciliary body 27 relieves excessive tension on the hyaloid zonules 39. This combined with returned control of the accommodative musculature will relieve excessive tension being transferred to the hyaloid retinal connections and thus reduce the risk of retinal detachment. The stent 47 requires specific sizing and anatomical placement, but has significant adjustment because its multi piece construction and O-ring 48 component. For example, it is possible to adjust the sizing of the stent 47 to induce forces to enable some manipulation of refractive error. The ocular stent 47 is positioned at the base of the cornea 32. This area of circumferential placement is the foundation of the cornea and, as such, the structural base of the cornea 32. The ability of stent 47 to articulate can enable it to harness and translate accommodative force to produce movement of the O-ring 48. This motion can be utilized to incorporate an accommodating anterior chamber interocular lens (ACIOL).

Figure 8A:
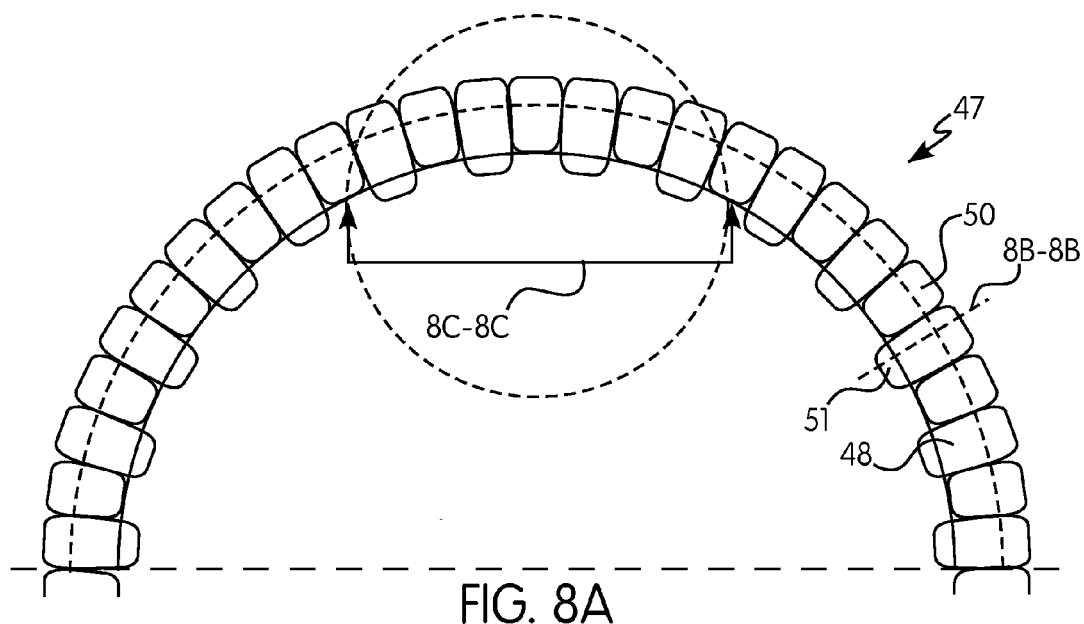
FIG. 8A is a half section front view of the stent of FIG. 7 as a multi-piece continuously joined ring with a continuous tensioning O-ring in place, in accordance with an aspect of the invention.

A half section front view of the stent 47 is shown in FIG. 8A. The stent 47 depicted in FIG. 8A illustrates the continuous beading together of the alternating anterior arm 50 and posterior arm 51 components. Placement of the O-ring 48 is also illustrated. The alternation of the components produces voids, allowing for free aqueous flow throughout the ocular stent. This is an advantage with respect to freedom of flow more representative of the natural anatomy. In the case of pigment dispersion syndrome and pigmentary glaucoma, this embodiment would not be the preferred one. This configuration cannot provide any pre-filtering properties as in the previously described embodiments of the stent. The alternating structure also serves the purpose of creating a non-continuous surface in contact with the transition zone 42 and iris base 29. The alternating pattern provides a variation of the appositional stimulation of stem cells.

Figure 8B:
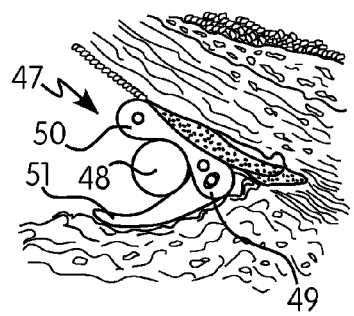
FIG. 8B is a cross-section view of the stent of FIG. 8A taken along section 8B-8B with illustrated anatomical detail shown, in accordance with an aspect of the invention.
Figure 8C:
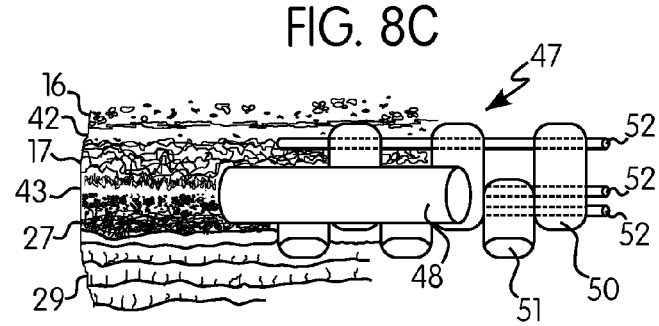
FIG. 8C is a partial side profile view of the stent of FIG. 8A taken along section 8C-8C with anatomical detail shown as it would be seen in the irideocorneal angle by means of gonioscopy, in accordance with an aspect of the invention.
Figure 8D:
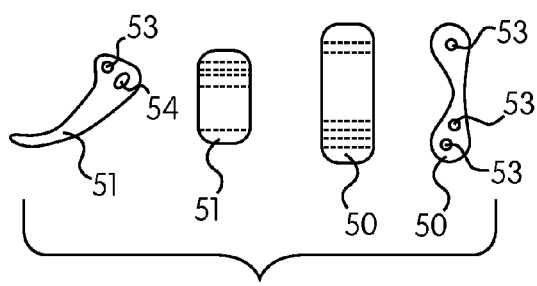
FIG. 8D is a schematic drawing that illustrates details of the articulating components of the stent of FIG. 8A, in accordance with an aspect of the present invention.

FIGS. 8B and 8C are schematic views of the stent 47 in situ with illustrative anatomy. The relationship between the O-ring 48, the anterior arm 50, the posterior arm 51 and anatomy is shown for the purpose of relating to FIG. 8C. FIG. 8C is a partial side profile view of the stent 47 as it would be viewed from inside the anterior chamber of the eye with anatomy visible. The stent 47 has the advantage of leaving some of the anatomy visible through the voids. It is noted that all of the embodiments of the stent described herein can be viewed by gonioscopy; however, the stent 47 depicted in FIGS. 7-8D has the most anatomy visible. The partial side view of the components has been staggered to illustrate the relationship between the components. This view best illustrates that the beading lines 52 tie the components together. As shown in FIG. 8C, three beading lines 52 are required to assemble the components. The triplication provides security that this embodiment will remain intact once assembled. FIG. 8D illustrates side and front views of the anterior arm 50 and posterior arm 51 separated as individual units. The holes used for beading are shown. The anterior arm 50 has three round holes 53, while the posterior arm has two round holes 53 and one slotted hole 54. The purpose of the slotted hole 54 is to allow articulating but limit range of motion. Such a limit on the range of motion is required to prevent the ocular stent from folding in on itself during implantation. The arms of the ocular stent 47 must remain open enough to insert the O-ring 48.

Figure 9A:
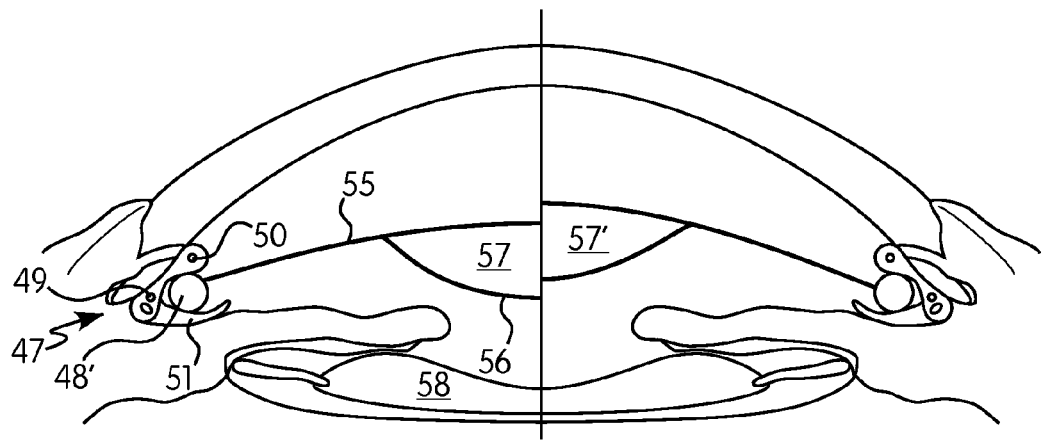
FIG. 9A is a schematic section view of an aphakic eye illustrating the stent of FIG. 7 in situ with an accommodating anterior chamber interocular lens (ACIOL) and an adjunctive stationary posterior chamber interocular lens (PCIOL), in accordance with an aspect of the invention.

FIG. 9A is a sectional view of an aphakic eye illustrating the stent 47 with an articulating joint 49. The implantation of an accommodating ACIOL is illustrated as it would be implanted and fit to the stent 47. The ACIOL body 57 illustrates the positioning of the ACIOL when the accommodative musculature is relaxed and 57' illustrates the ACIOL's change in position and curvature under accommodative stimulus. Articulation of the posterior arm 51 translates the accommodative contractions into small amounts of movement of the O-ring 48'. The O-ring 48' is incorporated into the ACIOL design becoming the peripheral limits of the ACIOL. The O-ring 48' is circumferentially fused with the extended anterior surface 55 of the ACIOL. The ACIOL has its optical form completed by its posterior surface 56. The two surfaces of the accommodating ACIOL could be manufactured from acrylic material that is then filled with index matched silicone oil or material of similar properties. These material properties will enable the vaulted ACIOL to change curvature with minor movement. Model tests and calculations indicate a decrease in diameter of 200 microns would potentially induce 10 diopters of accommodation. The refractive power of the ACIOL will need to be greater than the power of the human lens to produce sufficient levels of accommodation. In order to create an effective optical system of the appropriate total power a PCIOL 58 of opposing power will be required to complete this dual optic design.

Figure 9B:
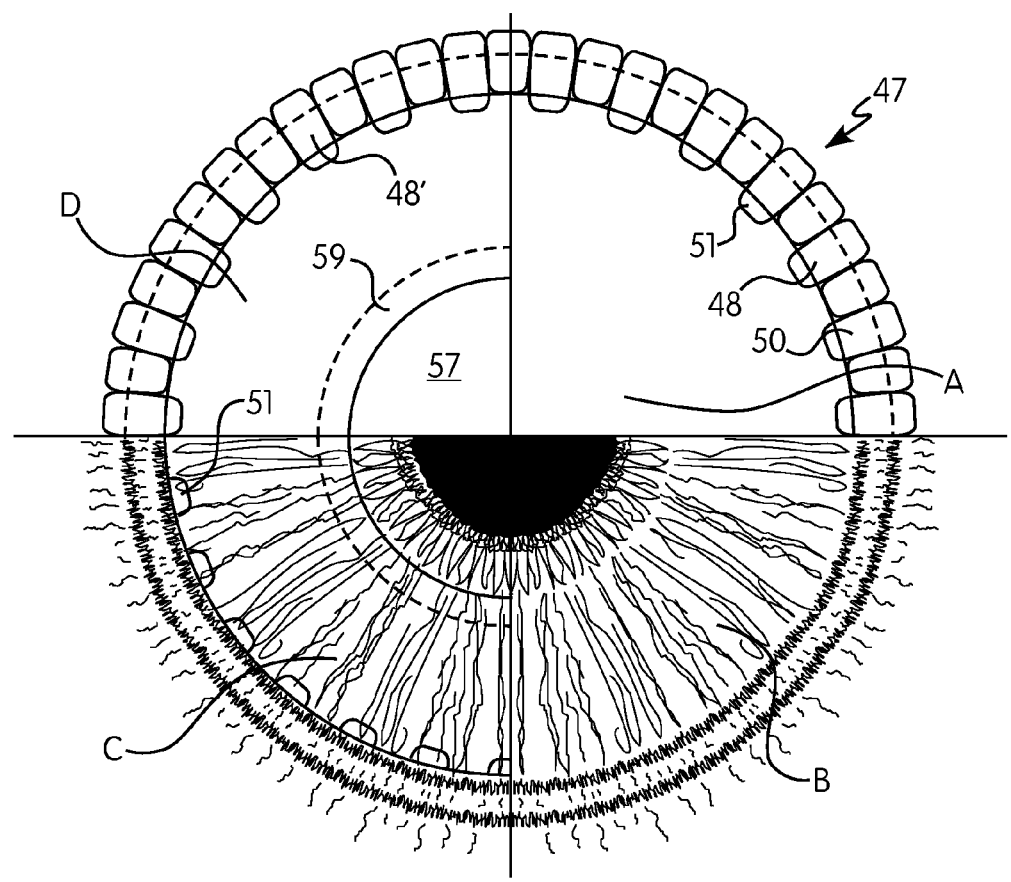
FIG. 9B is a schematic drawing of a quartered front view of an eye illustrating the various details of the stent of FIG. 7 and ocular anatomy, in accordance with an aspect of the invention.

FIG. 9B illustrates frontal view of the anatomy and the stent 47 with an accommodating ACIOL. The view is divided into quarters A, B, C, D. The first quarter A illustrates this embodiment independent of any anatomy. The alternating anterior arms 50 and posterior arms 51 along with the O-ring 48 are visible. The second quarter B represents the ocular anatomy without any stents implanted. The third quarter C illustrates the complete system of the stent 47 and the accommodation ACIOL components. Components visible would include partial views of the anterior 50 and posterior 51 arms. Although predominantly clear, the body of the ACIOL 57 and its anterior 55 and posterior 56 surfaces would be in view. The fourth quarter D has the complete assembly of components illustrated with the anatomy removed. An artificial pupil ring is indicated by 59. Because the optics of the ACIOL are anterior to the natural pupil it is optically advantageous to create a boundary between the refractive and non refractive aspects of the ACIOL.

Figure 10A:
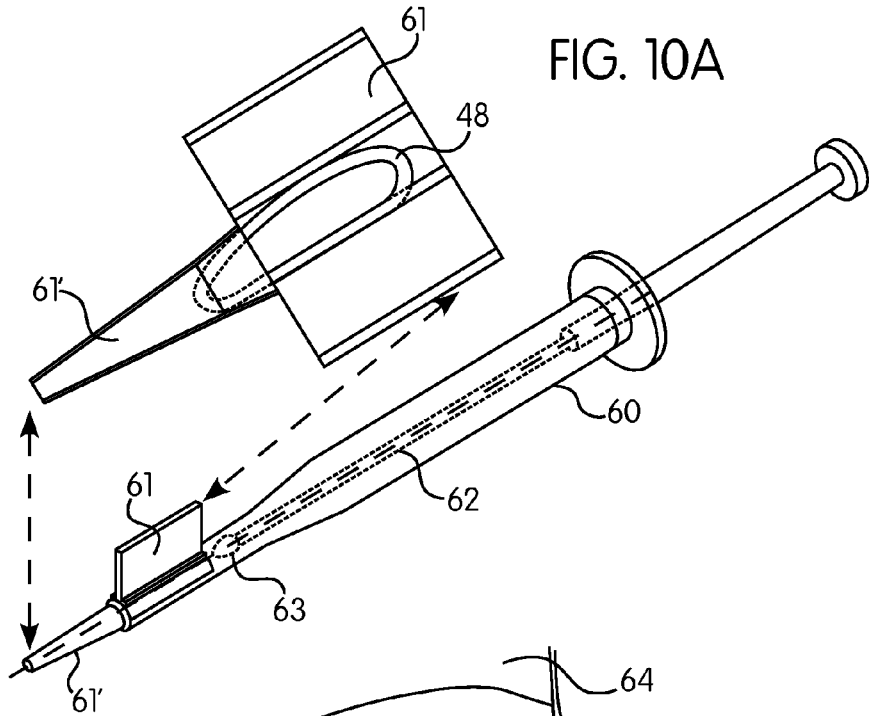
FIG. 10A is a schematic drawing of a folding interocular lens injector, which can be utilized for implantation of a stent, in accordance with an aspect of the invention.

FIG. 10A is an exemplary injector. Generally, the injector consists of a main body 60 that houses the plunger mechanism 62. The plunger has a silicon stopper 63, which is required to create the hydraulic pressure of the viscoelastic gliding agent used to eject the folded stent 18, 47 and/or the folded O-ring 48 from the chamber. The injector cartridge 61 opens allowing the ocular stent 18, 47 to be positioned carefully and flooded with viscoelastic before folding. In this illustration the O-ring 48 is being prepared for implantation. It may be required to push part of the O-ring 48 in to the cartridge tip 61' prior to folding. This will depend on the length of the cartridge tip 61'.

Figure 10B:
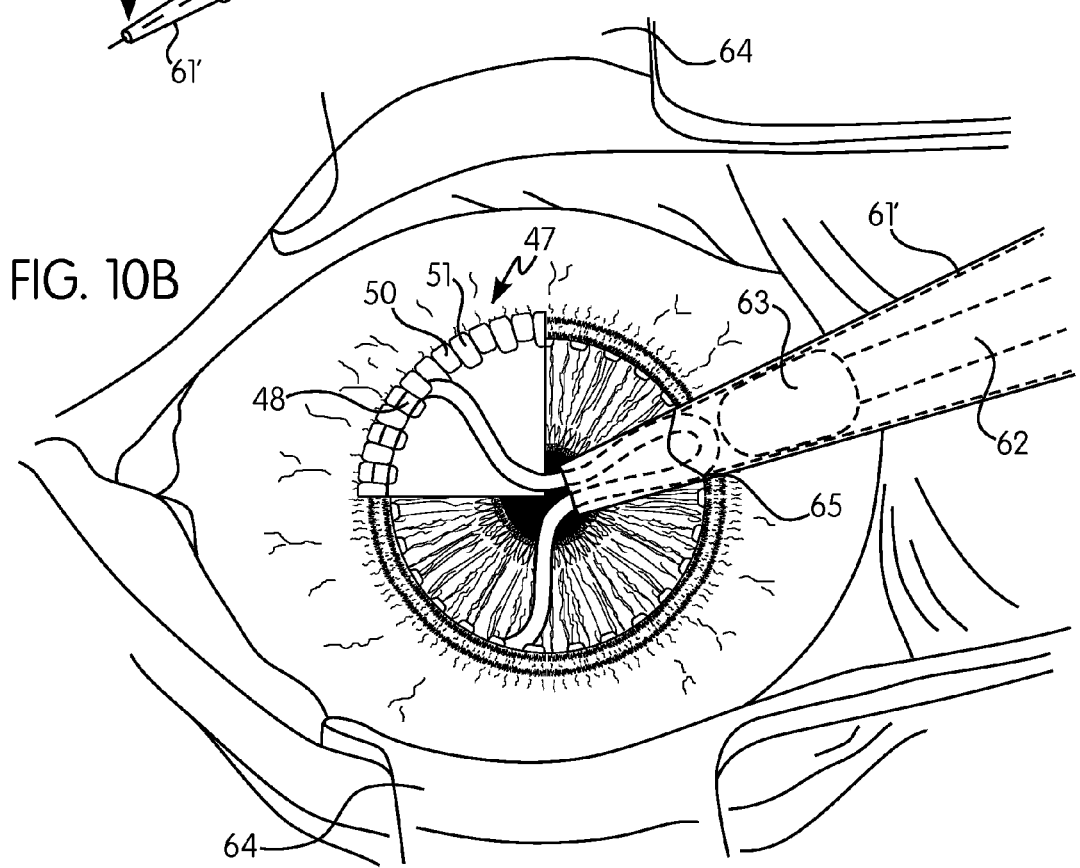
FIG. 10B is a schematic drawing of a front view of an implantation procedure, using the injector of FIG. 10A to inject a stent, in accordance with an aspect of the present invention.

In FIG. 10B a front view of the implantation procedure is illustrated. Here the eye has been prepared with eyelid speculums 64 in place and the incision wound 65 made. This illustration shows the stent 47 with its base structure already implanted. The anterior 50 and posterior 51 arms are partially visible in the anatomy, but clearly visible in the section where the anatomy has been removed for illustrative purposes. The O-ring 48 is seen as it is ejected from the cartridge tip 61'. The plunger 62 and the silicone stopper 63 creating the hydraulic viscoelastic pressure are also visible.

Discussion of this invention is made in relation to the human eye, but it is appreciated that the invention described herein is not limited or exclusive of the human eye. While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof. Further, although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An annular ocular stent for insertion in an irideocorneal angle of an anterior chamber of an eye comprising:
    a plurality of anterior arms configured to contact a surface of a transition zone between a trabecular meshwork and a corneal endothelium of the eye; and
    a plurality of posterior arms configured to contact a peripheral iris of the eye,
    a central portion connecting the anterior arms and the posterior arms to form an articulating joint with the central portion being a point of rotation, thereby defining an interior angle and an exterior angle, the exterior angle being commensurate with and configured to fit within the irideocorneal angle of the eye; and
    an o-ring adjacent to and receivable within the interior angle defined by the anterior and posterior arms.

2. The stent of claim 1, wherein the central portion comprises an annular cord, wherein at least one of the posterior arms and the anterior arms defines at least one through hole and wherein the cord is inserted therethrough, thereby connecting the at least one arm to the cord.

3. The stent of claim 2, wherein at least one of the through holes is a slotted through hole for limiting the range of motion of the joint.

4. The stent of claim 2, wherein the anterior arms and the posterior arms alternate along the one cord.

5. The stent of claim 1, wherein the plurality of anterior arms are also configured to contact at least a portion of an anterior portion of the trabecular meshwork.

6. The stent of claim 1, wherein the plurality of anterior arms comprise a plurality of crenellations extending therefrom, the crenellations being configured to create non-continuous contact with the transition zone.

7. The stent of claim 1, wherein a portion of each of the plurality of posterior arms is configured to extend around the irideocorneal angle and cross an anterior chamber exposure of a ciliary body up to or beyond a scleral spur of the eye.

8. The stent of claim 1, wherein the plurality of posterior arms are configured to be in contact with a portion of a surface of the peripheral iris.

9. The stent of claim 1, wherein the plurality of anterior arms and the plurality of posterior arms comprise one or more of: polymethylmethacrylate (PMMA), silicone or acrylic block polymers materials having PMMA components, hydrophobic acrylics, hydrophilic acrylics, acrylic poly(styrene-block-isobutylene-block-styrene), silicon elastomer, and heparin surface modified acrylics.

10. The stent of claim 1, wherein the plurality of anterior arms and the plurality of posterior arms comprise a shape memory material.

11. The stent of claim 1, further comprising an anterior chamber interocular lens coupled with the o-ring.

* * * * *